(12) United States Patent
Hunter

(10) Patent No.: US 9,333,060 B2
(45) Date of Patent: May 10, 2016

(54) PLAQUE REMOVAL AND DIFFERENTIATION OF TOOTH AND GUM

(75) Inventor: Ian W. Hunter, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 753 days.

(21) Appl. No.: 12/969,111

(22) Filed: Dec. 15, 2010

(65) Prior Publication Data

US 2011/0311939 A1 Dec. 22, 2011

Related U.S. Application Data

(60) Provisional application No. 61/286,632, filed on Dec. 15, 2009, provisional application No. 61/286,651, filed on Dec. 15, 2009.

(51) Int. Cl.
*A61C 17/02* (2006.01)
*A61C 19/06* (2006.01)

(52) U.S. Cl.
CPC ............... *A61C 17/02* (2013.01); *A61C 19/063* (2013.01)

(58) Field of Classification Search
CPC .... A61C 17/00; A61C 17/02; A61C 17/0202; A61C 19/04; A61H 23/04
USPC ......... 601/154, 155, 159, 160–163, 164, 165, 601/166; 433/80, 88–90, 98–100, 215, 216
See application file for complete search history.

(56) References Cited

U.S. PATENT DOCUMENTS

| 2,194,535 A | 3/1940 | Von Delden |
| 2,550,053 A | 4/1951 | Ferguson |

(Continued)

FOREIGN PATENT DOCUMENTS

| DE | 201 05 183 U1 | 6/2002 |
| DE | 101 46 535 A | 4/2003 |

(Continued)

OTHER PUBLICATIONS

Definition "Stream" Merriam-Webster Dictionary http://www.merriam-webster.com/dictionary/stream p. 1 of 1.*

(Continued)

*Primary Examiner* — Justin Yu
*Assistant Examiner* — LaToya M Louis
(74) *Attorney, Agent, or Firm* — Hamilton, Brook, Smith and Reynolds, P.C.

(57) ABSTRACT

A method of tooth treatment includes sensing a surface condition of tooth or gum and controlling ejection of a fluid jet against the tooth based on the sensed condition. The fluid may be a liquid and may be carried in a self-contained reservoir in a handle of a fluid ejection device. The liquid can be a cleansing solution and may contain cleaning particles. The ejection can be controlled to clean teeth at high pressure and to reduce pressure applied to gum, for example, to clean plaque. In some embodiments, the method may be used to remove soft tooth. The method may further include automatically scanning the fluid jet relative to a handle of an injection device. In an embodiment, the fluid is ejected by means of a fluid ejector comprising a stationary magnet assembly providing a magnetic field and a coil assembly, slidably disposed with respect to the magnet assembly, the coil assembly driving ejection of the fluid jet. Sensing the surface condition can include measuring a response of tissue to a mechanical perturbation and may include sensing an acoustic signal reflected from tissue. The mechanical perturbation can include applied force and the measured response can include deformation of the tissue. The method may further include mechanically disturbing the tissue with the fluid jet. A tooth treatment device includes a fluid ejector that ejects fluid against teeth and a servo controller controlling pressure of ejected fluid in response to a sensed surface condition. The fluid jet can have a diameter of less than 500 microns, a peak relative pressure of at least 1 kilopascal and velocity of at least 1 meter per second.

73 Claims, 13 Drawing Sheets

(56) References Cited

U.S. PATENT DOCUMENTS

| | | | | |
|---|---|---|---|---|
| 2,754,818 | A | 7/1956 | Scherer | |
| 2,928,390 | A | 3/1960 | Venditty et al. | |
| 3,057,349 | A | 10/1962 | Tsmach | |
| 3,309,274 | A | 3/1967 | Brilliant | |
| 3,574,431 | A | 4/1971 | Henderson | |
| 3,624,219 | A | 11/1971 | Perlitsh | |
| 3,659,600 | A | 5/1972 | Merrill | |
| 3,788,315 | A | 1/1974 | Laurens | |
| 3,810,465 | A * | 5/1974 | Lambert | 601/160 |
| 3,815,594 | A | 6/1974 | Doherty | |
| 3,923,060 | A | 12/1975 | Ellinwood, Jr. | |
| 3,973,558 | A * | 8/1976 | Stouffer et al. | 601/165 |
| 3,977,402 | A | 8/1976 | Pike | |
| 4,071,956 | A | 2/1978 | Andress | |
| 4,097,604 | A | 6/1978 | Thiele | |
| 4,103,684 | A | 8/1978 | Ismach | |
| 4,108,177 | A | 8/1978 | Pistor | |
| 4,122,845 | A * | 10/1978 | Stouffer et al. | 601/160 |
| 4,206,769 | A | 6/1980 | Dikstein | |
| 4,214,006 | A | 7/1980 | Thiele | |
| 4,215,144 | A | 7/1980 | Thiele | |
| 4,348,378 | A | 9/1982 | Kosti | |
| 4,431,628 | A | 2/1984 | Gaffar | |
| 4,435,173 | A | 3/1984 | Siposs et al. | |
| 4,447,225 | A | 5/1984 | Taff et al. | |
| 4,552,559 | A | 11/1985 | Donaldson et al. | |
| 4,592,742 | A | 6/1986 | Landau | |
| 4,744,841 | A | 5/1988 | Thomas | |
| 4,777,599 | A | 10/1988 | Dorogi et al. | |
| 4,886,499 | A | 12/1989 | Cirelli et al. | |
| 5,054,502 | A | 10/1991 | Courage | |
| 5,074,843 | A | 12/1991 | Dalto et al. | |
| 5,092,901 | A | 3/1992 | Hunter et al. | |
| 5,116,313 | A | 5/1992 | McGregor | |
| 5,242,408 | A | 9/1993 | Jhuboo et al. | |
| 5,244,461 | A | 9/1993 | Derlien | |
| 5,268,148 | A | 12/1993 | Seymour | |
| 5,277,200 | A | 1/1994 | Kawazoe et al. | |
| 5,318,522 | A | 6/1994 | D'Antonio | |
| 5,347,186 | A | 9/1994 | Konotchick | |
| 5,354,273 | A | 10/1994 | Hagen | |
| 5,389,085 | A | 2/1995 | D'Alessio et al. | |
| 5,405,614 | A | 4/1995 | D'Angelo et al. | |
| 5,425,715 | A | 6/1995 | Dalling et al. | |
| 5,478,328 | A | 12/1995 | Silverman et al. | |
| 5,479,937 | A | 1/1996 | Thieme et al. | |
| 5,480,381 | A | 1/1996 | Weston | |
| 5,505,697 | A | 4/1996 | McKinnon, Jr. et al. | |
| 5,533,995 | A | 7/1996 | Corish et al. | |
| 5,578,495 | A | 11/1996 | Wilks | |
| 5,611,784 | A | 3/1997 | Barresi et al. | |
| 5,622,482 | A | 4/1997 | Lee | |
| 5,694,920 | A | 12/1997 | Abrams et al. | |
| 5,722,953 | A | 3/1998 | Schiff et al. | |
| 5,795,153 | A * | 8/1998 | Rechmann | 433/216 |
| 5,820,373 | A | 10/1998 | Okano et al. | |
| 5,840,062 | A | 11/1998 | Gumaste et al. | |
| 5,865,795 | A | 2/1999 | Schiff et al. | |
| 5,879,312 | A | 3/1999 | Imoto | |
| 5,879,327 | A | 3/1999 | Moreau DeFarges et al. | |
| 5,919,167 | A | 7/1999 | Mulhauser et al. | |
| 6,004,287 | A | 12/1999 | Loomis et al. | |
| 6,030,399 | A | 2/2000 | Ignotz et al. | |
| 6,037,682 | A | 3/2000 | Shoop et al. | |
| 6,048,337 | A | 4/2000 | Svedman | |
| 6,056,716 | A | 5/2000 | D'Antonio et al. | |
| 6,074,360 | A | 6/2000 | Haar et al. | |
| 6,090,790 | A | 7/2000 | Eriksson | |
| 6,123,684 | A | 9/2000 | Deboer et al. | |
| 6,126,629 | A | 10/2000 | Perkins | |
| 6,132,385 | A | 10/2000 | Vain | |
| 6,152,887 | A | 11/2000 | Blume | |
| 6,155,824 | A * | 12/2000 | Kamen et al. | 433/80 |
| 6,164,966 | A | 12/2000 | Turdiu et al. | |
| 6,203,521 | B1 | 3/2001 | Menne et al. | |
| 6,272,857 | B1 | 8/2001 | Varma | |
| 6,288,519 | B1 | 9/2001 | Peele | |
| 6,317,630 | B1 | 11/2001 | Gross et al. | |
| 6,319,230 | B1 | 11/2001 | Palasis et al. | |
| 6,375,624 | B1 | 4/2002 | Uber, III et al. | |
| 6,375,638 | B2 | 4/2002 | Nason et al. | |
| 6,408,204 | B1 | 6/2002 | Hirschman | |
| 6,485,300 | B1 | 11/2002 | Muller et al. | |
| 6,565,532 | B1 | 5/2003 | Yuzhakov et al. | |
| 6,611,707 | B1 | 8/2003 | Prausnitz et al. | |
| 6,626,871 | B1 | 9/2003 | Smoliarov et al. | |
| 6,656,159 | B2 | 12/2003 | Flaherty | |
| 6,673,033 | B1 | 1/2004 | Sciulli et al. | |
| 6,678,556 | B1 | 1/2004 | Nolan et al. | |
| 6,723,072 | B2 | 4/2004 | Flaherty et al. | |
| 6,743,211 | B1 | 6/2004 | Prausnitz et al. | |
| 6,770,054 | B1 | 8/2004 | Smolyarov et al. | |
| 6,939,323 | B2 | 9/2005 | Angel et al. | |
| 7,032,443 | B2 | 4/2006 | Moser | |
| 7,270,543 | B2 | 9/2007 | Stookey et al. | |
| 7,425,204 | B2 | 9/2008 | Angel et al. | |
| 7,530,975 | B2 | 5/2009 | Hunter | |
| 7,645,263 | B2 | 1/2010 | Angel et al. | |
| 7,833,189 | B2 * | 11/2010 | Hunter et al. | 604/68 |
| 7,916,282 | B2 * | 3/2011 | Duineveld et al. | 356/72 |
| 8,105,270 | B2 | 1/2012 | Hunter | |
| 8,172,790 | B2 | 5/2012 | Hunter et al. | |
| 8,328,755 | B2 | 12/2012 | Hunter et al. | |
| 8,398,583 | B2 | 3/2013 | Hunter et al. | |
| 8,740,838 | B2 | 6/2014 | Hemond et al. | |
| 8,758,271 | B2 * | 6/2014 | Hunter et al. | 600/587 |
| 8,821,434 | B2 | 9/2014 | Hunter et al. | |
| 8,992,466 | B2 | 3/2015 | Hunter et al. | |
| 2002/0029924 | A1 | 3/2002 | Courage | |
| 2002/0055552 | A1* | 5/2002 | Schliesman et al. | 523/160 |
| 2002/0055729 | A1 | 5/2002 | Goll | |
| 2002/0095124 | A1 | 7/2002 | Palasis et al. | |
| 2002/0145364 | A1 | 10/2002 | Gaide et al. | |
| 2003/0065306 | A1 | 4/2003 | Grund | |
| 2003/0073931 | A1 | 4/2003 | Boecker et al. | |
| 2003/0083645 | A1 | 5/2003 | Angel et al. | |
| 2003/0153844 | A1 | 8/2003 | Smith et al. | |
| 2003/0207232 | A1 | 11/2003 | Todd et al. | |
| 2004/0010207 | A1 | 1/2004 | Flaherty et al. | |
| 2004/0065170 | A1* | 4/2004 | Wu et al. | 75/10.13 |
| 2004/0094146 | A1 | 5/2004 | Schiewe et al. | |
| 2004/0106893 | A1 | 6/2004 | Hunter | |
| 2004/0106894 | A1 | 6/2004 | Hunter et al. | |
| 2004/0143213 | A1 | 7/2004 | Hunter et al. | |
| 2004/0260234 | A1 | 12/2004 | Srinivasan et al. | |
| 2005/0022806 | A1 | 2/2005 | Beaumont et al. | |
| 2005/0170316 | A1 | 8/2005 | Russell et al. | |
| 2005/0287490 | A1 | 12/2005 | Stookey et al. | |
| 2006/0115785 | A1 | 6/2006 | Li et al. | |
| 2006/0258986 | A1* | 11/2006 | Hunter et al. | 604/164.01 |
| 2007/0055200 | A1 | 3/2007 | Gilbert | |
| 2007/0111166 | A1 | 5/2007 | Dursi | |
| 2007/0129693 | A1* | 6/2007 | Hunter et al. | 604/294 |
| 2007/0154863 | A1 | 7/2007 | Cai et al. | |
| 2007/0191758 | A1 | 8/2007 | Hunter et al. | |
| 2007/0248932 | A1* | 10/2007 | Gharib et al. | 433/81 |
| 2007/0275347 | A1* | 11/2007 | Gruber | 433/80 |
| 2008/0009788 | A1 | 1/2008 | Hunter et al. | |
| 2008/0027575 | A1 | 1/2008 | Jones et al. | |
| 2008/0060148 | A1 | 3/2008 | Pinyayev et al. | |
| 2008/0126129 | A1 | 5/2008 | Manzo | |
| 2008/0183101 | A1 | 7/2008 | Stonehouse et al. | |
| 2009/0017423 | A1* | 1/2009 | Gottenbos et al. | 433/216 |
| 2009/0056427 | A1 | 3/2009 | Hansma et al. | |
| 2009/0081607 | A1* | 3/2009 | Frey | 433/82 |
| 2009/0240230 | A1 | 9/2009 | Azar et al. | |
| 2010/0004624 | A1 | 1/2010 | Hunter | |
| 2010/0143861 | A1* | 6/2010 | Gharib et al. | 433/81 |
| 2011/0054354 | A1 | 3/2011 | Hunter et al. | |
| 2011/0054355 | A1 | 3/2011 | Hunter et al. | |
| 2011/0143310 | A1 | 6/2011 | Hunter | |
| 2011/0166549 | A1 | 7/2011 | Hunter et al. | |
| 2011/0311939 | A1 | 12/2011 | Hunter | |
| 2012/0003601 | A1 | 1/2012 | Hunter et al. | |

(56) References Cited

U.S. PATENT DOCUMENTS

| | | | |
|---|---|---|---|
| 2012/0089114 | A1 | 4/2012 | Hemond et al. |
| 2012/0095435 | A1 | 4/2012 | Hunter et al. |
| 2013/0102957 | A1 | 4/2013 | Hunter et al. |
| 2014/0257236 | A1 | 9/2014 | Hemond et al. |
| 2015/0025505 | A1 | 1/2015 | Hunter et al. |
| 2015/0051513 | A1 | 2/2015 | Hunter et al. |

FOREIGN PATENT DOCUMENTS

| | | | |
|---|---|---|---|
| EP | 0 599 940 B1 | | 12/1997 |
| EP | 0 834 330 A2 | | 4/1998 |
| EP | 1 020 200 A2 | | 7/2000 |
| EP | 0 710 130 B1 | | 12/2000 |
| EP | 1 514 565 A1 | | 3/2005 |
| GB | 686343 | | 1/1953 |
| GB | 756957 | | 9/1956 |
| GB | 2307860 | A | 6/1997 |
| JP | 06-327639 | A | 11/1994 |
| JP | 10-314122 | A | 12/1998 |
| JP | 2001-046344 | A | 2/2001 |
| JP | 2001-212087 | A | 8/2001 |
| JP | 2004-085548 | A | 3/2004 |
| JP | 2004-239686 | A | 8/2004 |
| JP | 2005-87722 | | 4/2005 |
| JP | 2005-5376834 | A | 12/2005 |
| JP | 5284962 | B | 6/2013 |
| WO | WO 91/16003 | A1 | 10/1991 |
| WO | WO 93/3779 | A1 | 3/1993 |
| WO | WO 95/7722 | A1 | 3/1995 |
| WO | WO 98/08073 | A1 | 2/1998 |
| WO | WO 00/23132 | A1 | 4/2000 |
| WO | WO 01/26716 | A1 | 4/2001 |
| WO | WO 01/37907 | A1 | 5/2001 |
| WO | WO 03/035149 | A1 | 5/2003 |
| WO | WO 03/039635 | A2 | 5/2003 |
| WO | WO 03/068296 | A2 | 8/2003 |
| WO | WO 03/086510 | A1 | 10/2003 |
| WO | WO 2004/021882 | A2 | 3/2004 |
| WO | WO 2004/022138 | A2 | 3/2004 |
| WO | WO 2004/022244 | | 3/2004 |
| WO | WO 2004/093818 | A2 | 4/2004 |
| WO | WO 2004/058066 | A1 | 7/2004 |
| WO | WO 2004/071936 | A2 | 8/2004 |
| WO | WO 2004/101025 | A2 | 11/2004 |
| WO | WO 2004/112871 | A1 | 12/2004 |
| WO | WO 2006/086720 | A2 | 8/2006 |
| WO | WO 2006/086774 | A2 | 8/2006 |
| WO | WO 2008001303 | A1 * | 1/2008 |
| WO | WO 2008/027579 | A1 | 3/2008 |
| WO | WO 2011/028716 | A1 | 3/2011 |
| WO | WO 2011/028719 | A2 | 3/2011 |
| WO | WO 2011/075535 | A1 | 6/2011 |
| WO | WO 2011/075545 | A1 | 6/2011 |
| WO | WO 2011/084511 | A1 | 7/2011 |
| WO | WO 2012/048268 | A2 | 4/2012 |
| WO | WO 2012/048277 | A2 | 4/2012 |

OTHER PUBLICATIONS

Definition "Stream" The Free Dictionary http://www.thefreedictionary.com/stream pp. 1-8.*
International Search Report and the Written Opinion of the International Searching Authority from International Application No. PCT/US2010/060554 dated Apr. 6, 2011.
International Search Report and the Written Opinion of the International Searching Authority from International Application No. PCT/US2010/060562 dated Apr. 6, 2011.
International Search Report and the Written Opinion of the International Searching Authority from International Application No. PCT/US2010/060608 dated Apr. 6, 2011.
Aguirre, A., et al., "Sialochemistry: A diagnostic tool", *Critical Reviews in Biology and Medicine*, 4: 343-350 (1993).
Amado, F.M.L., et al., "Analysis of the human saliva proteome", *Exp. Rev. Proteomics*, 2: 521-539 (2005).
Aps, J.K.M. and Martens, L.C., "Review: The physiology of saliva and transfer of drugs into saliva", *Forensic Sci. International*, 150: 119-131 (2005).
Baab, D.A., et al., "A comparison of antimicrobial activity of four disclosant dyes ", *J. Dental Res.*, 62: 837-841 (1983).
Baum, B. J., et al., "Salivary glands: novel target sites for gene therapeutics", *TRENDS Mol. Med.*, 10: 585-590 (2004).
Chen, Y. and Hunter I.W., "In vivo characterization of skin using a Wiener nonlinear stochastic identification method" *Proceedings of 31st Annual IEEE Engineering in Medicine and Biology Conference*, 6010-6013 (2009).
Daniluk, T., et al., "Aerobic and anaerobic bacteria in subgingival and supragingival plaques of adult patients with periodontal disease", *Adv. Med. Sci.*, 51: 81-85 (2006).
Kaufman, E. and Lamster, I.B., "The diagnostic applications of saliva—a review", *Crit. Rev. Oral Biol. Med.*, 13: 197-212 (2002).
Marcotte, H. and Lavoie, M. C., "Oral microbial ecology and the role of salivary immunoglobulin A", *Micro. Mol. Bio.*, 62(1): 71-109 (1998).
U.S. Appl. No. 12/712,824, filed Feb. 25, 2010.
U.S. Appl. No. 12/969,280, filed Dec. 15, 2010.
Wolf, H. and Hassell, T., "Plaque Disclosing Agents", *Color Atlas of Dental Hygiene: Periodontology*, p. 225 (2006).
International Preliminary Report on Patentability in International Application No. PCT/US2010/060554, 8 pages, mailed Jun. 19, 2012.
International Preliminary Report on Patentability in International Application No. PCT/US2010/060608, 7 pages, mailed Jun. 19, 2012.
International Preliminary Report on Patentability in International Application No. PCT/US2010/060562, 7 pages, mailed Jun. 19, 2012.
* Office Action in U.S. Appl. No. 12/969,280, dated Mar. 14, 2012.
Bischoff, J. E., et al., "Finite element modeling of human skin using an isotropic, nonlinear elastic constitutive model," *J. Biomech.*, 33: 645-652 (2000).
Boyer, G., et al., "Dynamic indentation on human skin in vivo: ageing effects," *Skin Research and Technology*, 15: 55-67 (2009).
Carter, F. J., et al., "Measurements and modelling of the compliance of human and porcine organs," *Medical Image Analysis*, 5: 231-236 (2001).
Chen, K., and Zhou, H., "An experimental study and model validation of pressure in liquid needle-free injection," *International Journal of the Physical Sciences*, 6(7): 1552-1562 (2011).
Chen, K., et al., "A Needle-free Liquid Injection System Powered by Lorentz-force Actuator." Paper presented at International Conference on Mechanic Automation and Control Engineering, Wuhan, China (Jun. 2010).
Chen, Y., and Hunter, I. W., "Nonlinear Stochastic System Identification of Skin Using Volterra Kernels," *Annals of Biomedical Engineering*, 41(4): 847-862 (2013).
Chen, Y., and Hunter, I. W., "Stochastic System Identification of Skin Properties: Linear and Wiener Static Nonlinear Methods," *Annals of Biomedical Engineering*, 40(10): 2277-2291 (2012).
Daly, C. H., and Odland, G. F., "Age-related Changes in the Mechanical Properties of Human Skin," *The Journal of Investigative Dermatology*, 73: 84-87 (1979).
Delalleau, A., et al., "A nonlinear elastic behavior to identify the mechanical parameters of human skin in vivo," *Skin Research and Technology*, 14: 152-164 (2008).
Diridollou, S., et al., "An In Vivo Method for Measuring the Mechanical Properties of the Skin Using Ultrasound," *Ultrasound in Med. & Biol.*, 24(2): 215-224 (1998).
Diridollou, S., et al., "Sex- and site-dependent variations in the thickness and mechanical properties of human skin in vivo," *Int. J. Cosmetic Sci.*, 22: 421-435 (2000).
Escoffier, C., et al., "Age-Related Mechanical Properties of Human Skin: An In Vivo Study," *J. Invest. Dermatol.*, 93: 353-357 (1989).
Flynn, D. M., et al., "A Finite Element Based Method to Determine the Properties of Planar Soft Tissue," *J. Biomech. Eng.—T. ASME*, 120(2): 202-210 (1998).

(56) References Cited

OTHER PUBLICATIONS

Garcia-Webb, M. G., et al., "A modular instrument for exploring the mechanics of cardiac myocytes," *Am. J. Physiol. Heart Circ. Physiol.*, 293: H866-H874 (2007).

Goussard, Y., et al., "Practical Identification of Functional Expansions of Nonlinear Systems Submitted to Non-Gaussian Inputs," *Ann. Biomed. Eng.*, 19: 401-427 (1991).

Hartzshtark, A., and Dikstein, S., "The use of indentometry to study the effect of agents known to increase skin c-AMP content," *Experientia*, 41: 378-379 (1985).

He, M. M., et al., "Two-Exponential Rheological Models of the Mechanical Properties of the Stratum Corneum," *Pharmaceutical Research*, 13(9): S1-S604 (1996).

Hemond, B. D., et al., "A Lorentz-Force Actuated Autoloading Needle-free Injector," *Proceedings of the 28th IEEE EMBS Annual International Conference*, 679-682 (2006).

Hemond, B.D., et al., "Development and Performance of a Controllable Autoloading Needle-Free Jet Injector", *J. Med. Dev.*, Mar. 2011, vol. 5, pp. 015001-1 through 015001-7.

Hendricks, F. M., et al., "A numerical-experimental method to characterize the non-linear mechanical behavioue of human skin," *Skin Research and Technology*, 9: 274-283 (2003).

Hirota, G., et al., "An Implicit Finite Element Method for Elastic Solids in Contact," *Proceedings on the Fourteenth Conference on Computer Animation*, 136-146 (2001).

Hunter, I. W., and Kearney, R. E., "Generation of Random Sequences with Jointly Specified Probability Density and Autocorrelation Functions," *Biol. Cybern.*, 47: 141-146 (1983).

Hunter, I. W., and Korenberg, M. J., "The Identification of Nonlinear Biological Systems: Wiener and Hammerstein Cascade Models," *Biol. Cybern.*, 55: 135-144 (1986).

Jachowicz, J., et al., "Alteration of skin mechanics by thin polymer films," *Skin Research and Technology*, 14: 312-319 (2008).

Khatyr, F., et al., "Model of the viscoelastic behaviour of skin in vivo and study of anisotropy," *Skin Research and Technology*, 10: 96-103 (2004).

Korenberg, M. J., and Hunter, I. W., "The Identification of Nonlinear Biological Systems: LNL Cascade Models," *Biol. Cybern.*, 55: 125-134 (1986).

Korenberg, M. J., and Hunter, I. W., "The Identification of Nonlinear Biological Systems: Volterra Kernel Approaches," *Annals of Biomedical Engineering*, 24: 250-268 (1996).

Korenberg, M. J., and Hunter, I. W., "Two Methods for Identifying Wiener Cascades Having Noninvertible Static Nonlinearities," *Annals of Biomedical Engineering*, 27: 793-804 (1999).

Lee, Y. W., and Schetzen, M., "Measurement of the Wiener Kernels of a Non-linear System by Cross-correlation," *Int. J. Control*, 2(3): 237-254 (1965).

Lindahl, O. A., et al., "A tactile sensor for detection of physical properties of human skin in vivo," *J. Med. Eng. Technol.*, 22(4): 147-153 (1998).

Lu, M.-H., et al., "A Hand-Held Indentation System for the Assessment of Mechanical Properties of Soft Tissues In Vivo," *IEEE Transactions on Instrumentation and Measurement*, 58(9): 3079-3085 (2009).

Manschot, J. F. M., and Brakkee, A. J. M., "The Measurement and Modelling of the Mechanical Properties of Human Skin In Vivo—I. The Measurement," *J. Biomech.*, 19(7): 511-515 (1986).

Manschot, J. F. M., and Brakkee, A. J. M., "The Measurement and Modelling of the Mechanical Properties of Human Skin In Vivo—II. The Model," *J. Biomech.*, 19(7): 517-521 (1986).

Menciassi, A., et al., "An Instrumented Probe for Mechanical Characterization of Soft Tissues," *Biomed. Microdevices*, 3(2): 149-156 (2001).

Oka, H., and Irie, T., "Mechanical impedance of layered tissue," *Medical Progress through Technology*, Suppl. 21: 1-4 (1997).

Ottensmeyer, M. P., and Salisbury, J. K., Jr., "In Vivo Data Acquisition Instrument for Solid Organ Mechanical Property Measurement," *Lecture Notes in Computer Science*, 2208: 975-982 (2001).

Patton, R. L., "Mechanical Compliance Transfer Function Analysis for Early Detection of Pressure Ulcers." Bachelor's thesis, Massachusetts Institute of Technology (1999).

Post, E. A., "Portable Sensor to Measure the Mechanical Compliance Transfer Function of a Material." Bachelor's thesis, Massachusetts Institute of Technology (2006).

Potts, R. O., et al., "Changes with Age in the Moisture Content of Human Skin," *The Journal of Investigative Dermatology*, 82(1): 97-100 (1984).

Reihsner, R., et al., "Two-dimensional elastic properties of human skin in terms of an incremental model at the in vivo configuration," *Med. Eng. Phys.*, 17: 304-313 (1995).

Sandford, E., et al., "Capturing skin properties from dynamic mechanical analyses," *Skin Research and Technology*, 0: 1-10 (2012).

Soong, T. T., and Huang, W. N., "A Stochastic Model for Biological Tissue Elasticity," *Proceedings of the Fourth Canadian Congress of Applied Mechanics*, 853-854 (1973).

Stachowiak, J. C., et al., "Dynamic control of needle-free jet injection", *J. Controlled Rel.*, 135:104-112 (2009).

Taberner, A.J., et al., "A Portable Needle-free Jet Injector Based on a Custom High Power-density Voice-coil Actuator", *Proceedings of the 28th IEEE, EMBS Annual International Conference*, Aug. 30-Sep. 3, 2006, pp. 5001-5004.

Taberner, et al., "Needle-free jet injection using real-time controlled linear Lorentz-force actuators," *Med. Eng. Phys.*, (2012) doi: 10.1016/j.medengphy.2011.12.010.

Tosti, A., et al., "A Ballistometer for the Study of the Plasto-Elastic Properties of Skin," *The Journal of Investigative Dermatology*, 69: 315-317 (1977).

Zahouani, H., et al., "Characterization of the mechanical properties of a dermal equivalent compared with human skin in vivo by indentation and static friction tests," *Skin Research and Technology*, 15: 68-76 (2009).

Zhang, M., and Roberts, V. C., "The effect of shear forces externally applied to skin surface on underlying tissues," *J. Biomed. Eng.*, 15(6): 451-456 (1993).

\* cited by examiner

PLAQUE REMOVAL AND DIFFERENTIATION OF TOOTH AND GUM

RELATED APPLICATIONS

This application claims the benefit of U.S. Provisional Application No. 61/286,632, filed on Dec. 15, 2009, and U.S. Provisional Application No. 61/286,651, filed on Dec. 15, 2009. The entire teachings of the above applications are incorporated herein by reference.

BACKGROUND OF THE INVENTION

In the oral cavity, indigenous bacteria are often associated with two major oral diseases; caries and periodontitis [H. Marcotte and M. C. Lavoie, Oral microbial ecology and the role of salivary immunoglobulin A, Micro Mol Bio 62 (1998) 71-109]. The diverse structures within the mouth (i.e. the tooth surface, subgingival space, and tongue) support several different microbial communities. The supragingival environment of the oral cavity is regulated by saliva, a complex mixture of water, electrolytes (e.g. sodium, potassium, calcium, chloride, magnesium, bicarbonate, phosphate), enzymes (e.g. lysozyme, lactoferrin, peroxidase), proteins (e.g. sIgA, glycoproteins etc.), vitamins, hormones, urea and nitrogenous products. The less accessible subgingival environment is bathed by the gingival crevicular fluid (GCF), a plasma exudate containing proteins, albumin, leukocytes, immunoglobulins, and complement.

Good oral hygiene requires that one sustain a healthy oral ecosystem. However, the boundaries between the soft mucosa and hard teeth are ripe for bacterial colonization (e.g. the gingival crevice or sulcus). The sulcus together with the area between the teeth (i.e. approximate surface), and the pits and fissures of the biting surface are not easily cleaned by brushing (i.e. mechanical friction). Microorganisms tend to colonize these areas to form dental plaque; a biofilm of microorganisms and salivary components. If not removed, plaque can lead to caries or periodontal disease (e.g. gingivitis and possibly periodontitis). Plaque and calculus can be removed with or without electrically driven hand instruments in the dental office. Calculus, a form of hardened plaque, forms along the gum line and within the sulcus leading to inflammation that can eventually lead to deep pockets between the teeth and gum and loss of bone that holds the tooth in place. Human periodontitis is associated with a widely diverse and complex subgingival microbiota [Daniluk, T., Tokajuk, G., Cylwik-Rokicka, D., Rozkiewics, D., Zaremba, M. L., and Stokowska, W., Aerobic and anaerobic bacteria in subgingival and supragingival plaques of adult patients with periodontal disease, Adv Med Sci 51: (2006) 81-85].

While there are commercially available water jet devices for dental cleaning, they are limited for the most part to the removal of debris. The pumps used in these units are often noisy, which can contribute to patient discomfort. Seating or mating the tip with the water jet is sometimes problematic leading to leakage and ineffective or less than optimal irrigation. While some devices have adjustable controls, many do not provide good control.

Sensing devices for diagnosing oral health and/or hygiene are currently either in the research and development stage or are formatted for use by trained professionals. Many devices are not user friendly and not suitable for day to day use by consumers.

SUMMARY OF THE INVENTION

A method of tooth treatment includes sensing a surface condition of tooth or gum and controlling ejection of a fluid jet against the tooth based on the sensed condition.

The fluid may be a liquid and may be carried in a self-contained reservoir in a handle of a fluid ejection device. The reservoir can be less than 100 milliliters. The liquid can be a cleansing solution and may contain cleaning particles.

In one embodiment, the fluid jet is of a diameter of less than 500 microns. The jet may be of a diameter of less than 200 microns. The ejection may be controlled at a bandwidth of at least 10 Hertz, of at least 50 Hertz, of at least 100 Hertz, or of at least 1 kilo Hertz. The fluid may be ejected at a peak relative pressure of at least 1 kilopascal or of at least 100 kilopascals, and at a velocity of at least 1 meter per second or of at least 10 meters per second. The ejection can be controlled to clean teeth at high pressure and to reduce pressure applied to gum and may be controlled to clean plaque. Less than 100 milliliters of liquid may be ejected per teeth cleaning session. In some embodiments, the method may be used to remove soft tooth. The method may further include automatically scanning the fluid jet relative to a handle of an injection device.

In an embodiment, the fluid is ejected by means of a fluid ejector comprising a stationary magnet assembly providing a magnetic field and a coil assembly, slidably disposed with respect to the magnet assembly, the coil assembly driving ejection of the fluid jet.

In some embodiments, sensing the surface condition includes measuring a response of tissue to a mechanical perturbation. The mechanical perturbation can include applied force and the measured response can include deformation of the tissue. The method may further include mechanically disturbing the tissue with the fluid jet. Measuring a response of the tissue may include measuring pressure of the fluid. Measuring pressure can include sensing strain of a fluid reservoir and may include sensing position of an actuator driving the ejection of the fluid. In an embodiment, sensing the surface condition includes sensing an acoustic signal reflected from tissue. The acoustic signal may travels through the fluid jet and may be sensed using a piezo-electric transducer. The method may further include generating the acoustic signal. The acoustic signal may be generated and sensed using a piezo-electric transducer, and may include a stochastic signal. Further, sensing the surface condition may include measuring tissue deformation with applied force using the sensed acoustic signal. The force can be applied using the fluid jet. In some embodiments, the method may further include sensing motion of a fluid ejector and controlling the ejection of the fluid jet based on the sensed motion.

A method of tooth treatment includes ejecting a fluid jet against the tooth, the jet having a diameter of less than 500 microns, a peak relative pressure of at least 1 kilopascal and velocity of at least 1 meter per second. The method may be used for removing plaque from teeth and may include automatically scanning the fluid jet relative to a handle of an injection device.

A hand-held tooth treatment device includes a housing configured to be held on hand and a fluid ejector positioned at an end of the housing that ejects fluid against teeth in a scanning movement relative to the housing. The scan may be greater than 1 millimeter. The device may further include a servo controller controlling pressure of ejected fluid in response to a sensed surface condition, such as a mechanical property of tissue. Further, the device can include a pressure sensor that senses pressure of the fluid in the ejector. The pressure sensor may include a strain gauge that senses strain of a reservoir of the ejector. Alternatively or in addition, the pressure sensor can include a position sensor that senses position of an actuator driving the ejection of the fluid. The device may further include a distance sensor that senses distance of the ejector from a tissue surface. In some embodiments, the distance sensor includes a piezo-electric transducer and the distance is sensed using an acoustic signal. Further, the device may include a servo controller controlling pressure of ejected fluid in response to a sensed motion of the ejector.

A method of tooth treatment includes ejecting a fluid jet against the tooth and scanning the fluid jet relative to a handle of an injection device. Further, the method of tooth treatment can include controlling pressure of ejected fluid based on a sensed surface condition and, alternatively or in addition, based on a sensed motion of the injection device. The method may be used for removing plaque from tooth.

A tooth treatment device includes a fluid ejector that ejects fluid against teeth and a servo controller controlling pressure of ejected fluid in response to a sensed surface condition. The device may further include a housing configured to be held on hand, the fluid ejector being positioned at an end of the housing. Further, the device can include a self-contained reservoir of the liquid in the housing and the reservoir may be less than 100 milliliters. In some embodiments, the device may further include a pressure sensor that senses pressure of the fluid in the ejector, and wherein the surface condition is sensed based on the sensed pressure. Alternatively or in addition, the device may further include an acoustic transducer that senses an acoustic signal reflected off tissue, and wherein the surface condition is sensed based on the reflected acoustic signal.

A tooth treatment device includes a fluid ejector that ejects a fluid jet against the tooth, the jet having a diameter of less than 500 microns, a peak relative pressure of at least 1 kilopascal and velocity of at least 1 meter per second.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
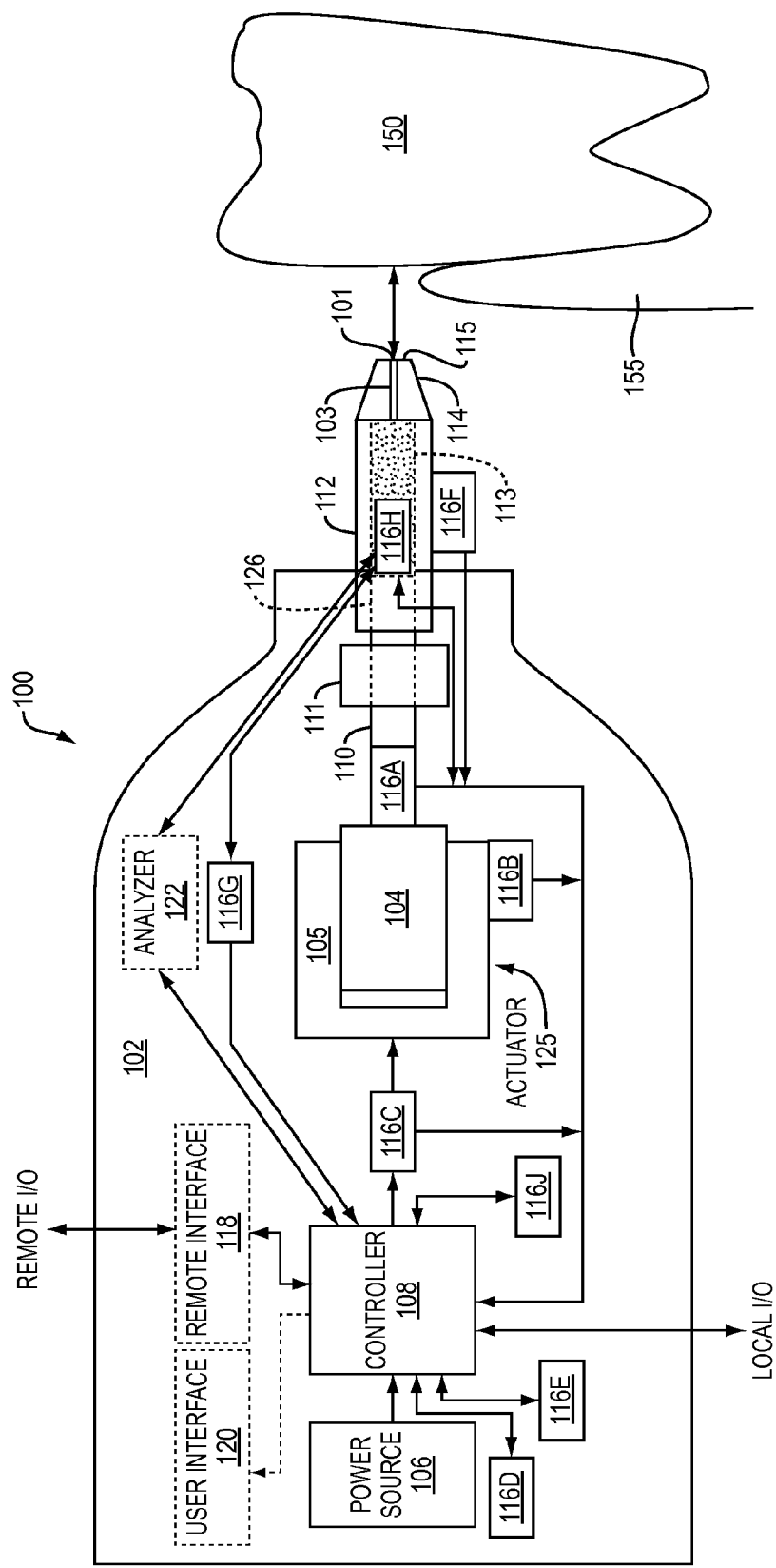
FIG. 1 is a schematic block diagram of one embodiment of a controllable, needle-free transfer device for cleaning teeth, gums, and other areas of the mouth.

A description of example embodiments of the invention follows.

The entire teachings of U.S. patent application Ser. No. 10/277,722, filed on Oct. 21, 202, entitled "Impedance Sensor" now U.S. Pat. No. 7,645,263, issued on Jan. 12, 2010; U.S. Pat. No. 6,939,323, issued on Sep. 6, 2005, entitled "Needleless Injector"; U.S. Pat. No. 7,425,204, issued on Sep. 16, 2008, entitled "Needleless Injector"; U.S. patent application Ser. No. 12/459,866, filed on Jul. 8, 2009, entitled "Bi-Directional Motion of a Lorentz-Force Actuated Needle-Free Injector (NFI)"; U.S. Pending patent application Ser. No. 12/872,630, filed on Aug. 31, 2010, entitled "Nonlinear System Identification Techniques and Device For Discovering Dynamic And Static Tissue Properties"; U.S. Pat. No. 7,530,975, issued on May 12, 2009, entitled "Measuring Properties of an Anatomical Body"; and U.S. Published Application No. US 2007/0191758, published on Aug. 16, 2007, entitled "Controlled Needle-Free Transport" are incorporated herein by reference. These Applications and Patents relate to sensors and injectors that may be utilized in implementing the present invention.

Embodiments of the present invention relate to a needle-free device for cleaning the teeth, the gums, and other areas of the mouth. The embodiments of the present invention may be used for cleaning and diagnosis of dental and medical conditions in human or animals. Certain embodiments include a fine jet injector that transfers high pressured liquid (e.g., water, liquid designed for cleaning of the mouth, liquid designed for diagnosis of medical or dental conditions, and etc.) to remove and blast off plaque from the human teeth. The jet injector is servo-controlled to transfer the liquid and control the pressure of the fluid in the vicinity of soft tissue (e.g., gums). As such, the high pressure liquid will remove plaque from the teeth without penetrating the gums. The device may operate in real time by determining mechanical properties of the transfer site and distinguish between hard tissue and soft tissue based on the mechanical properties.

The needle-free device includes an actuator capable of generating a high-speed, high-pressure pulse that is both controllable and highly predictable. The device may be combined with a servo-controller receiving inputs from one or more sensors. Further, the device may adjust or tailor the pressure profile of a transfer in real-time, during the course of the transfer, responsive to sensed physical properties of tissue and teeth. For example, the device may be able to distinguish soft tissue (e.g., gums, gum lines, and tongue) from the teeth.

The jet injector may include sensors that detect respective physical properties of the transfer site. The physical properties can be used to servo control the jet injector and tailor the injection pressure, and, therefore, the depth of penetration of fluid into for a particular region. For instance, when the device is used on the gums, the sensor detects the softness of the gums, and the controller uses the properties of the gums and consequently reduces the transfer pressure. The transfer pressure can be adjusted, for example, by controlling the electrical input signal applied to the injector and/or the current pulse rise time and/or duration. When used on hard enamel (teeth), the controller may increase the transfer pressure. The transfer pressure may be adjusted depending on location of the liquid transfer, for example, the gums versus the tongue. The transfer pressure can also be tailored to deliver a substance just underneath the gum line or deep into gums. Moreover, the transfer pressure may be varied over time.

Since oral plaque is usually stored as deep as one millimeter under the gum line, the controller of the needle-free device can distinguish between the teeth, gums, and the gum line by considering the physical properties of the teeth and the soft tissue and adjust the transfer pressure on each of these body parts accordingly.

In certain embodiments, the needle-free injector generates a jet pressure and transfers high pressure liquid that can remove the plaque from the teeth. The peak liquid pressure may be as low as 1 Kilo Pascal. In some embodiments up to 100 Kilo Pascal of relative water pressure may be applied.

Jets of less than 500 microns are generally employed. In certain embodiments, very fine jets may be employed. For example, jets having diameter of less than five micro meters may be employed. In one embodiment, the jet injectors may have a diameter of less than 200 micrometers.

The needle-free device is servo-controlled to transfer the fluid and control the pressure of the fluid in the vicinity of soft tissue (e.g., gums) and the teeth. Due to the high level of control offered by the device, the amount of fluid transferred into the mouth may be significantly reduced. In some embodiments, a tooth cleaning liquid having appropriate cleaning agents may be jet injected into the mouth, teeth, or the gums to help with blasting of plaque and maintaining oral health. Additional substances may be included in the liquid injected into the mouth. For example, substances having bacteria and fungus fighting agents, whitening agents, or breath freshening agents may be employed.

In some embodiments, the needle-free device may further include one or more electrical impedance sensors that can be used to distinguish between soft tissue (gums and tongue) and the teeth. The impedance testing also provides a convenient way of determining the depth of penetration. The impedance sensor may include an electrode positioned to measure the impedance of a portion of the target area between the electrode and ground to indicate the depth of penetration into the target area.

In certain embodiments, two or more jet injectors may be employed with one of the jet injectors serving as a ground connection for impedance measurements. In some embodiments, a conductive fluid can be used for cleaning or diagnosis. In these embodiments, the body, through the lip, when it comes in contact with the injector, provides the ground connection for the impedance measurements.

In some embodiments, the needle-free device includes a reservoir for storing the fluid and a controllable electromagnetic actuator in communication with the reservoir. The controllable electromagnetic actuator may include a stationary magnet assembly providing a magnetic field; and a coil assembly. The coil assembly receives an electrical input and generates in response a force corresponding to the received input. The force results from interaction of an electrical current within the coil assembly and the magnetic field and causes the transfer of the fluid between the reservoir and the mouth. The needle-free device can include a sensor that senses physical properties of the transfer site and causes the servo-controller to generate the electrical input responsive to the sensed physical property. In order to measure the physical properties, ranging techniques using acoustic waves or laser beams may be applied to find deformation of teeth or gum lines. Acoustic waves may be used in combination with a fluid jet, where the pressure of the fluid jet applies a force to the target tissue to perturb the target tissue and the acoustic waves are used to sense the deformation or displacement of the tissue in response to the perturbation. The acoustic signal can propagate through the fluid jet and may include a sinusoidal and/or stochastic signal.

Example embodiments may include a Lorentz-Force actuator to provide reversibility for the device. In such embodiments, a fluid can be pumped into the mouth to blast off and remove plaque and the removed material may then be removed from the mouth using the reversible actuator. The Lorentz force actuator exerts a force. The force can be used for needle-free transfer of the substance between the reservoir and the mouth. The injector can determine changes in response to the forces and determine individual target area properties based on the response to the forces. In certain embodiments, stochastic (random) or pseudo-random information can be employed to create a model (e.g., non-parametric model) of tissue properties.

Example embodiments may include a piezoelectric actuator to provide high frequency pulses of the fluid jet. The device may have a minimum bandwidth of approximately 10 Hz (Hertz). In certain embodiments the device may have a bandwidth of 50 Hz, 100 Hz, or 100 KHz.

Certain embodiments may include sensors and related technologies for analyzing materials removed from the mouth such as plaque, saliva, and etc. The analyzed results may be used to distinguish between healthy and unhealthy tissue in the mouth. In some embodiments, the liquid transferred into the mouth may include biomarkers for verifying oral health and detecting possible health issues. In some embodiments, the same liquid containing biomarkers may be used in cleaning and plaque removal.

In some embodiments, the needle-free device may be used in diagnosis of oral conditions. For example, the device may be used to determine if a tooth has a cavity or is decaying. Since the mechanical properties of a decaying tooth are different from that of a healthy tooth, the device can diagnose a decaying tooth by determining a change in the mechanical property of the tooth. Microelectromechanical Systems (MEMS) along with accelerometers may be used to determine the location of a decaying tooth.

The device may be coupled to a Computer-Aided Diagnosis model of the mouth to determine health status of every surface. The device may transfer a fluid that is to be used on a daily basis for cleaning and a second fluid for diagnosis that is to be used on a less frequent basis. Certain embodiments may employ Raman spectroscopy techniques to distinguish healthy and unhealthy tissue. The data obtained regarding the health of the mouth may be fed into a database, or transferred, possibly via a wireless module, for further evaluation or analysis.

The device may transfer as much as 10 microliters of fluid, e.g., liquid, per second. The liquid may be transferred at a peak pressure of 1 kilo Pascal to loosen food. In certain embodiments, an average pressure of up to 100 Mega Pascal may be used to loosen plaque. The device may operate at a velocity as low as 1 meter per second (m/s). In some embodiments, velocities as high as 10 m/s or higher (e.g., ⅔ of the speed of sound) may be used.

Pulses can be used to dynamically control (e.g., servo-control) the magnitude, direction and duration of the force during the course of an actuation cycle. In certain embodiments, the device includes an actuator capable of generating a high-speed, high-pressure pulse that is both controllable and highly predictable. The device also includes the ability to pulse shape to use different waveforms for each cycle. In certain embodiments, fine sinusoidal pulses may be employed to approximate a square wave. For example, a sinusoidal pulse having a bandwidth of 10 microseconds can be used.

The device may be coupled to multiple reservoirs. In one example embodiment, the device includes two reservoirs arranged such that one reservoir includes a larger amount of fluid compared to the other reservoir. At each cycle, a square wave is used to control the direction and duration of the force. At each cycle a certain amount of fluid is transferred from the second reservoir into the mouth. At the end of the cycle, a limited amount of liquid is transferred from the first reservoir into the second reservoir.

The device may also be used in drilling the teeth. Previously, dentists removed cavity by simply feeling soft, unhealthy enamel from the teeth (while removing healthy enamel in the process). The device can determine the mechanical properties of healthy tooth vs. unhealthy tooth and use a combination of velocity and pressure coupled with an abrasive to drill the unhealthy portion of the tooth and leave the healthy enamel behind. Drill heads as small as 50 micrometers in diameter may be used.

FIG. 1 is a schematic block diagram of a needle-free transport device or jet injector 100 that may be used in example embodiments. Device 100 can transfer a substance to or from a surface of a biological body and may be used to eject a fluid against tooth 150, gum 155, or other tissue in the oral cavity. The jet injector 100 can be used to deposit a fluid, including a medicant or biomarker, into the space between tooth 150 and gum 155. Alternatively of in addition, the same device can be used to collect a sample from a location at or near the tooth 150 or gum 155 by withdrawing the collected sample into a reservoir 113

The device 100 typically includes a nozzle 114 to convey the substance. Namely, substance ejected from the nozzle 114 forms a jet, the force of the jet determining the depth of penetration. The nozzle 114 generally contains a flat surface, such as the head 115 and an orifice 101. It is the inner diameter of the orifice 101 that controls the diameter of the transferred stream. Additionally, the length of an aperture or tube 103, defining the orifice 101 also controls the transfer (e.g., injection) pressure.

The nozzle 114 can be coupled to a reservoir 113 for temporarily storing the transferred substance. Reservoir 113 may be a reservoir of a syringe or ampoule 112. Beneficially, a pressure is selectively applied to the reservoir 113 using a controllable actuator. A specially-designed electromagnetic actuator 125 is configured to generate a high-pressure pulse having a rapid rise time (e.g., less than 1 millisecond). The actuator 125 can be used in needle-free injection devices that rely on high-pressure actuators to inject a formulation beneath the skin. The actuator is dynamically controllable, allowing for adjustments to the pressure-versus-time during actuation. At least one advantage of the electromagnetic actuator over other needle-free devices is its relatively quiet operation. Actuation involves movement of a freely suspended coil within a gap, rather than the sudden release of a spring or the discharge of a gas. Actuation of the freely-moving coil in the manner described herein results in quiet operation, which is an important feature as it contributes to reducing pain and anxiety during administration to the recipient and to others that may be nearby.

In more detail, the electromagnetic actuator 125 is configured to provide a linear force applied to the plunger 126 to achieve transfer of the substance. Transfer of the force can be accomplished with a force-transfer member 110, such as a rigid rod slidably coupled through a bearing 111. The rod may be secured at either end such that movement of the actuator in either direction also moves the plunger 126. The bearing restricts radial movement of the rod 110, while allowing axial movement.

In some embodiments, the actuator 125 is a Lorentz force actuator that includes a stationary component, such as a magnet assembly 105, and a moveable component, such as a coil assembly 104. A force produced within the coil assembly 104 can be applied to the plunger 126 either directly or indirectly through the rod 110 to achieve transfer of the substance.

In some embodiments, device 100 may not include a separate bearing 111. Rather, an interior surface of the housing 102 provides a bearing for the coil assembly 104 allowing axial movement while inhibiting radial movement.

In some embodiments, the device 100 includes a user interface 120 that provides a status of the device. The user interface may provide a simple indication that the device is ready for actuation. More elaborate user interfaces 120 can be included to provide more detailed information, including a liquid crystal display (LCD), cathode ray tube (CRD), charge-coupled device (CCD), or any other suitable technology capable of conveying detailed information between a user and the device 100. Thus, user interface 120 may also contain provisions, such as a touch screen to enable an operator to provide inputs as user selections for one or more parameters. Thus, a user may identify parameters related to dose, sample, parameters related to the biological body, such as age, weight, etc.

A power source 106 provides an electrical input to the coil assembly 104 of the actuator 125. An electrical current applied to the coil assembly 104 in the presence of a magnetic field provided by the magnet assembly 105 will result in a generation of a mechanical force capable of moving the coil assembly 104 and exerting work on the plunger 126 of the syringe 112. The electromagnetic actuator is an efficient force transducer supporting its portability.

A controller 108 is electrically coupled between the power source 106 and the actuator 125, such that the controller 108 can selectively apply, withdraw and otherwise adjust the electrical input signal provided by the power source 106 to the actuator 125. The controller 108 can be a simple switch that is operable by a local interface. For example, a button provided on the housing 102 may be manipulated by a user, selectively applying and removing an electrical input from the power source 106 to the actuator 125. In some embodiments, the controller 108 includes control elements, such as electrical circuits, that are adapted to selectively apply electrical power from the power source 106 to the actuator 125, the electrical input being shaped by the selected application. Thus, for embodiments in which the power source 106 is a simple battery providing a substantially constant or direct current (D.C.) value, the electrical input can be shaped by the controller to provide a different or even time varying electrical value. In some embodiments, the controller 108 includes an on-board microprocessor, or alternatively an interconnected processor or personal computer providing multifunction capabilities. A power amplifier (not shown) may be included in the controller 108 or, alternatively or in addition, in power source 106.

In some embodiments, the needle-free device 100 includes a remote interface 118. The remote interface 118 can be used to transmit information, such as the status of the device 100 or of a substance contained therein to a remote source, such as a hospital computer or a drug manufacturer's database. Alternatively or in addition, the remote interface 118 is in electrical communication with the controller 108 and can be used to forward inputs received from a remote source to the controller 108 to affect control of the actuator 125.

The remote interface 118 can include a network interface, such as a local area network interface (e.g., Ethernet). Thus, using a network interface card, the device 100 can be remotely accessed by another device or user, using a personal computer also connected to the local area network. Alternatively or in addition, the remote interface 118 may include a wide-area network interface. Thus, the device 100 can be remotely accessed by another device or user over a wide-area network, such as the World-Wide Web. In some embodiments, the remote interface 118 includes a modem capable of interfacing with a remote device/user over a public-switched telephone network. In yet other embodiments, the remote interface 118 includes a wireless interface to access a remote device/user wirelessly. The wireless interface 118 may use a standard wireless interface, such as Wi-Fi standards for wireless local area networks (WLAN) based on the IEEE 802.11 specifications; new standards beyond the 802.11 specifications, such as 802.16 (WiMAX); and other wireless interfaces that include a set of high-level communication protocols such as ZigBee, designed to use small, low power digital radios based on the IEEE 802.15.4 standard for wireless personal area networks (WPANs).

In some embodiments the controller receives inputs from one or more sensors adapted to sense a respective physical property. For example, the device 100 includes a transducer, such as a position sensor 116B used to indicate location of an object's coordinates (e.g., the coil's position) with respect to a selected reference. Similarly, a displacement may be used to indicate movement from one position to another for a specific distance. Beneficially, the sensed parameter can be used as an indication of the plunger's position and therefore an indication of dose. In some embodiments, a proximity sensor may also be used to indicate when a part of the device, such as the coil, has reached a critical distance. This may be accomplished by sensing the position of the plunger 126, the force-transfer member 110, or the coil assembly 104 of the electromagnetic actuator 125. For example, an optical sensor such as an optical encoder can be used to count turns of the coil to determine the coil's position. Other types of sensors suitable for measuring position or displacement include inductive transducers, resistive sliding-contact transducers, photo-diodes, and linear-variable-displacement-transformers (LVDT).

Other sensors, such as a force transducer 116A can be used to sense the force applied to the plunger 126 by the actuator 125. As shown, a force transducer 116A can be positioned between the distal end of the coil assembly and the force transfer member 110, the transducer 116A sensing force applied by the actuator 125 onto the force-transfer member 110. As this member 110 is rigid, the force is directly transferred to the plunger 126. The force tends to move the plunger 126 resulting in the generation of a corresponding pressure within the reservoir 113. A positive force pushing the plunger 126 into the reservoir 113 creates a positive pressure tending to force a substance within the reservoir 113 out through the nozzle 114. A negative force pulling the plunger 126 proximally away from the nozzle 114 creates a negative pressure or vacuum tending to suck a substance from outside the device through the nozzle 114 into the reservoir 113. The substance may also be obtained from another reservoir or ampoule, the negative pressure being used to pre-fill the reservoir 113 with the substance. Alternatively or in addition, the substance may come from the biological body representing a sampling of blood, tissue, and or other interstitial fluids. In some embodiments, a pressure transducer (not shown) can also be provided to directly sense the pressure applied to a substance within the chamber or reservoir 113. In addition, the position sensor 116B may sense the position of the coil which may be used to indirectly measure the pressure within the reservoir 113.

An electrical sensor 116C may also be provided to sense an electrical input provided to the actuator 125. The electrical sensor may sense one or more of coil voltage and coil current. Other sensors may include for example a gyrometer 116D, an accelerometer 116E, a strain gauge 116F, a temperature sensor 116G, an acoustic sensor or transducer 116H, and/or barometric pressure sensor 116J. The gyrometer 116D may include a 3-axis gyroscope and the accelerometer 116E may include a 3-axis accelerometer. The sensors 116A, 116B, 116C, 116D, 116E, 116F, 116G, 116H, and 116J (generally 116) are coupled to the controller 108 providing the controller 108 with the sensed properties. The controller 108 may use one or more of the sensed properties to control application of an electrical input from the power source 106 to the actuator 125, thereby controlling pressure generated within the syringe 112 to produce a desired transfer performance. For example, a position sensor can be used to servo-control the actuator 125 to pre-position the coil assembly 104 at a desired location and to stabilize the coil 104 once positioned, and conclude an actuation cycle. Thus, movement of the coil assembly 104 from a first position to a second position corresponds to transfer of a corresponding volume of substance. The controller can include a processor programmed to calculate the volume based on position given the physical size of the reservoir.

An actuation cycle, generally corresponds to initiation of an electrical input to the actuator 125 to induce transfer of a substance and conclusion of the electrical input to halt transfer of the substance. A servo-control capability combined with the dynamically controllable electromagnetic actuator 125 enables adjustment of the pressure during the course of an actuation cycle. One or more of the sensors 116 can be used to further control the actuation cycle during the course of the transfer, or cycle. Alternatively or in addition, one or more of local and remote interfaces can also be used to further affect control of the actuation cycle.

In some implementations, the controller 108 is coupled with one or more sensors 116, or one or more other sensors (not shown), that detect respective physical properties of the biological body. This information can be used to servo control the actuator 125 to tailor the injection pressure. For instance, when the device 100 is used on the gums, the sensor detects the softness of the gums, and the controller 108 uses the properties of the gums and consequently reduces the injection pressure. The injection pressure can be adjusted, for example, by controlling the electrical input signal applied to the actuator 125 and/or the current pulse rise time and/or duration. When used on teeth, the controller may increase the injection pressure. The injection pressure may be adjusted depending on location of the skin on the body, for example, the face versus the arm of the patient. Moreover, the injection pressure may be varied over time. For instance, in some implementations, a large injection pressure is initially used to loosen cavity, and then a lower injection pressure is used to loosen food.

For example, the controller 108 may be coupled with an acoustic sensor 116I, such as a piezo-electric sensor or transducer, to measure the deformation of the biological body in response to a mechanical perturbation. The piezo-electric transducer may be located at the tip of the device, for example, at or near nozzle 114. The transducer may be in fluid communication with the fluid ejected through nozzle 114 and may also be in fluid communication with reservoir 113. In one embodiment, the piezo-electric transducer can be located at the distal end of plunger 126 (see FIG. 2A). The piezo-electric transducer may emit acoustic signals and sense acoustic signal reflected from the biological body. The acoustic signal may include a high-frequency and/or stochastic signal.

In more detail, the power source 106 can be external or internal to the device 100 or be rechargeable. The power source 106 can include a replaceable battery. Alternatively, the power source 106 includes a rechargeable device, such as a rechargeable battery (e.g., gel batteries; lead-acid batteries; Nickel-cadmium batteries; Nickel metal hydride batteries; Lithium ion batteries; and Lithium polymer batteries). In some embodiments, the power source 106 includes a storage capacitor. For example, a bank of capacitors can be charged through another power source, such as an external electrical power source.

In more detail, the electromagnetic actuator 125 includes a conducting coil assembly 104 disposed relative to a magnetic field, such that an electrical current induced within the coil results in the generation of a corresponding mechanical force. The configuration is similar, at least in principle, to that found in a voice coil assembly of a loud speaker. Namely, the relationship between the magnetic field, the electrical current and the resulting force is well defined and generally referred to as the Lorentz force law.

Preferably, the coil 104 is positioned relative to a magnetic field, such that the magnetic field is directed substantially perpendicular to the direction of one or more turns of the coil 104. Thus, a current induced within the coil 104 in the presence of the magnetic field results in the generation of a proportional force directed perpendicular to both the magnetic field and the coil (a relationship referred to as the "right hand rule").

Figure 2A:
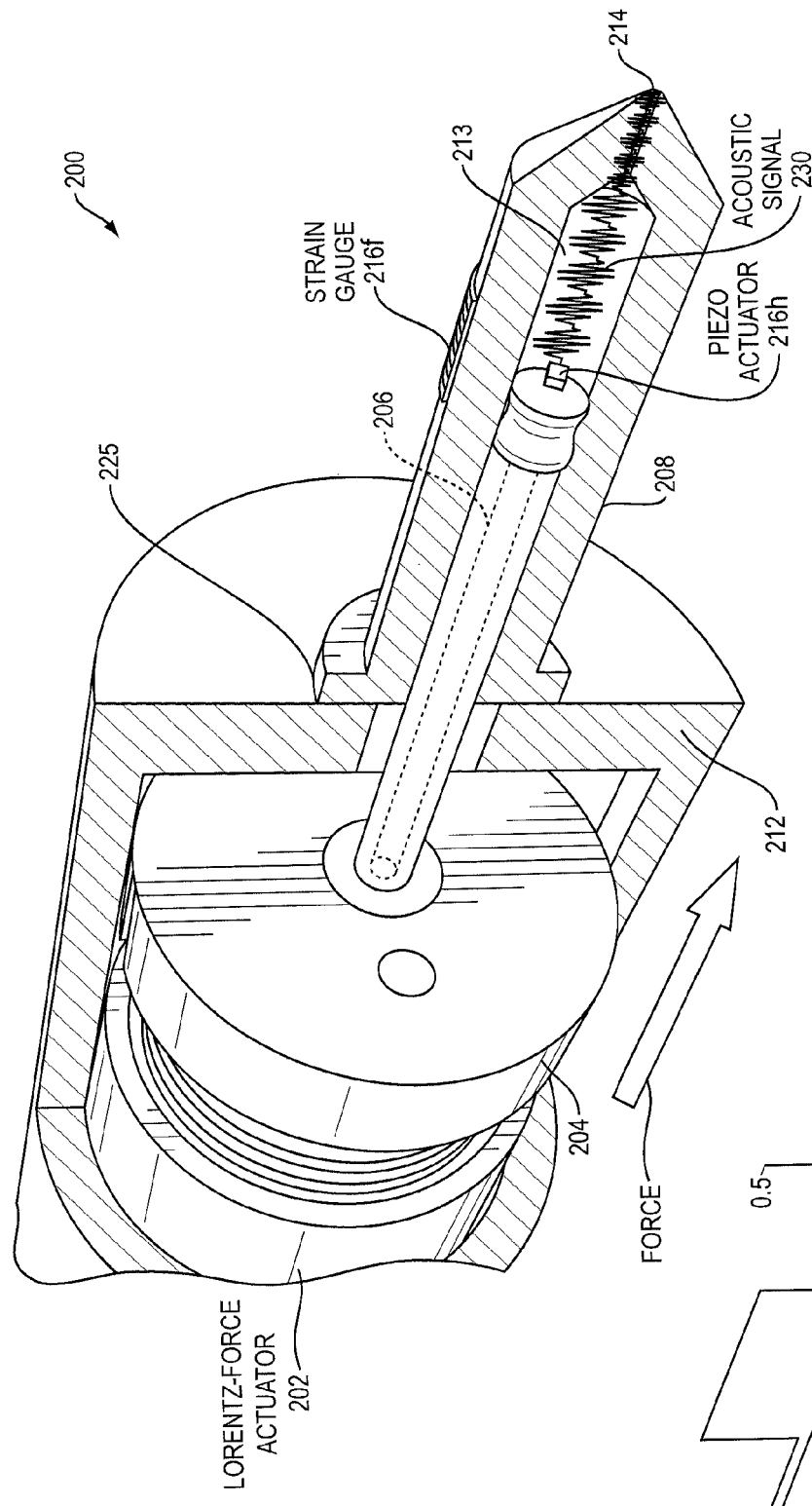
FIG. 2A is a partial cut-away perspective diagram of an embodiment of a controllable needle-free transfer device.

An exemplary embodiment of a dynamically-controllable needle-free injection device 200 is shown in FIG. 2A. The device 200 includes a compact electromagnetic actuator 202 having a distal force plate 204 adapted to abut a proximal end of a plunger 206 of a syringe or ampoule 208. The ampoule 208 may, for example, be a commercially available polycarbonate ampoule, such as the INJEX™ ampoule. The device 200 also includes a mounting member 212 to which a proximal end of the syringe 208 is coupled. A power source (not shown) may also be disposed proximal to the actuator 202, the different components being secured with respect to each other within a housing or shell 216. In some embodiments, a coupler 225 is provided to removably fasten the plunger 206 to the actuator 202. This ensures that the plunger is moved in either direction responsive to movement of the actuator 202.

Figure 2B:
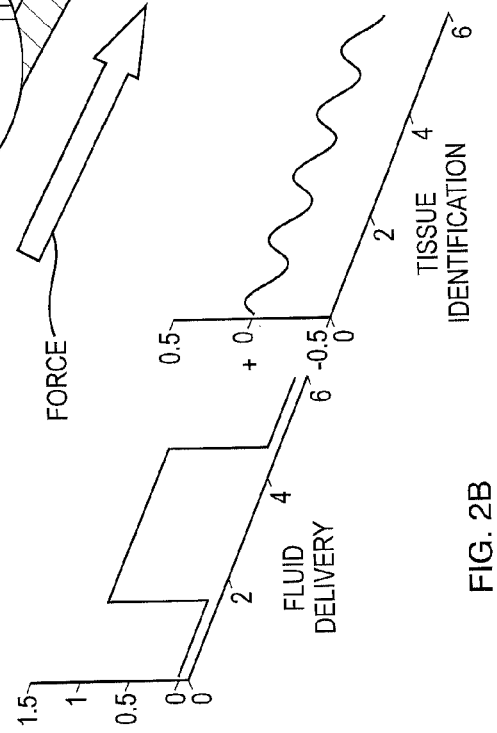
FIG. 2B are graphs depicting force-versus-time profiles of exemplary force components used for fluid delivery and for tissue identification, the force components being generated by the controllable electromagnetic actuator of FIG. 2A.

FIG. 2B are graphs depicting force-versus-time profiles of components of exemplary force applied to ... reservoir 213 in the transfer of a substance and in tissue identification, the force being generated by the controllable electromagnetic actuator of FIG. 2A. As shown, the actuator may apply a square-wave force component for fluid delivery that is modulated with a low frequency sinusoidal signal for tissue perturbation and identification. Alternative or in addition, the actuator may also apply a stochastic signal for tissue perturbations.

As shown in FIG. 2A, device 200 can include a piezoelectric actuator or transducer 216H located at the distal end of plunger 206. The transducer is in fluid communication with the fluid ejected through nozzle 214 and in fluid communication with reservoir 213 of ampoule 208. The piezo-electric transducer may emit acoustic signals 230 and sense acoustic signals reflected from the biological body, e.g., the tooth or gum. The acoustic signal may include a high-frequency and/or stochastic signal. The piezo-electric transducer may continuously send an acoustic signal through the fluid and sense the reflection of the signal off a target surface of the biological body. Information of the emitted and reflected signal can then be used to continuously determine the distance of the target surface from the transducer, and may be used to measure the displacement or deformation of the biological body.

Device 200 may include a strain gauge 216F and a position sensor or linear encoder 216B to sense fluid pressure, including back pressure from the ejection of the fluid against tissue, such as tooth, gum, or any other tissue or surface. Sensing pressure using the strain gauge and/or the position sensor can be used to measure the reaction of tissue to the sinusoidal signal modulating the fluid jet and may be used to sense a surface condition of the tissue.

Figure 3:
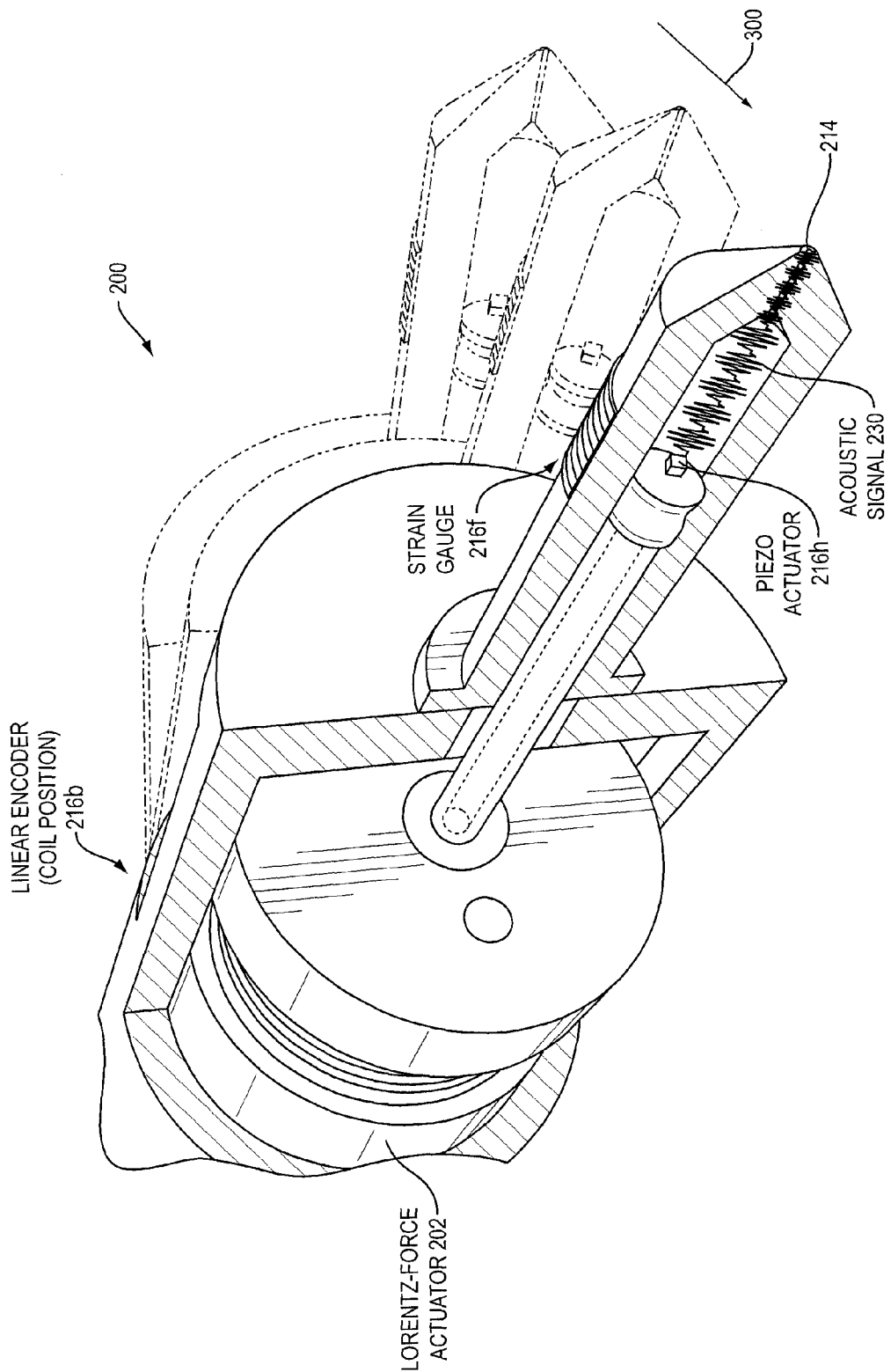
FIG. 3 is a partial cut-away perspective diagram of the device of FIG. 2A illustrating scanning of the device.

FIG. 3 is a partial cut-away perspective diagram of the device of FIG. 2A illustrating scanning of a fluid jet. The needle-free device 200 may operate as a hand-held device moving over the teeth, the gums, the tongue, or other parts of the mouth. The device may include multiple degrees of freedom to be able to scan the teeth from various positions and orientations. For example, the device 200 may scan the teeth in vertical or horizontal (e.g., left and right) directions. FIG. 3 illustrates scanning in a horizontal direction as indicated by the arrow 300. The needle-free device 200 is highly controllable in terms of pressure, flow, and velocity and can provide for linear, spiral, or rotary scans, resulting in multi-dimensional coverage of the mouth. The device 200 can eject a fluid against the teeth and the gum in a scanning motion, sense a surface condition, and control the ejection pressure based on the sense condition. For example, device 200 can control fluid ejection to scan with low pressure and, when on teeth, clean the surface of teeth with high pressure. The needle-free device 200 may also be used in cleaning the surface of the tongue since it can detect the softness of the tongue and vary its transfer pressure.

In one embodiment, the strain gauge 216F coupled to the ampoule 208 (FIG. 2A) is high sensitivity, high bandwidth strain gauge. An example of a suitable strain gauge is a general-purpose strain gauge made from constantan alloy having a resistance of 120 ohm and gauge factor of about 2. With a 2.5 V activation voltage, the strain gauge can achieve sensitivity of 5 µV/N and operate at a background noise level of 0.6 µV. Another example of a suitable strain gauge with higher sensitivity is a platinum-tungsten strain gauge having 350 ohm resistance and a gauge factor of about 4.5. The strain gauge may be coupled to a controller, such as a NATIONAL INSTRUMENTS™ NI CompactRIO Control and Acquisition System, to power the gauge and collect measurements at, for example, 25 k Sample/sec.

Figure 4A:
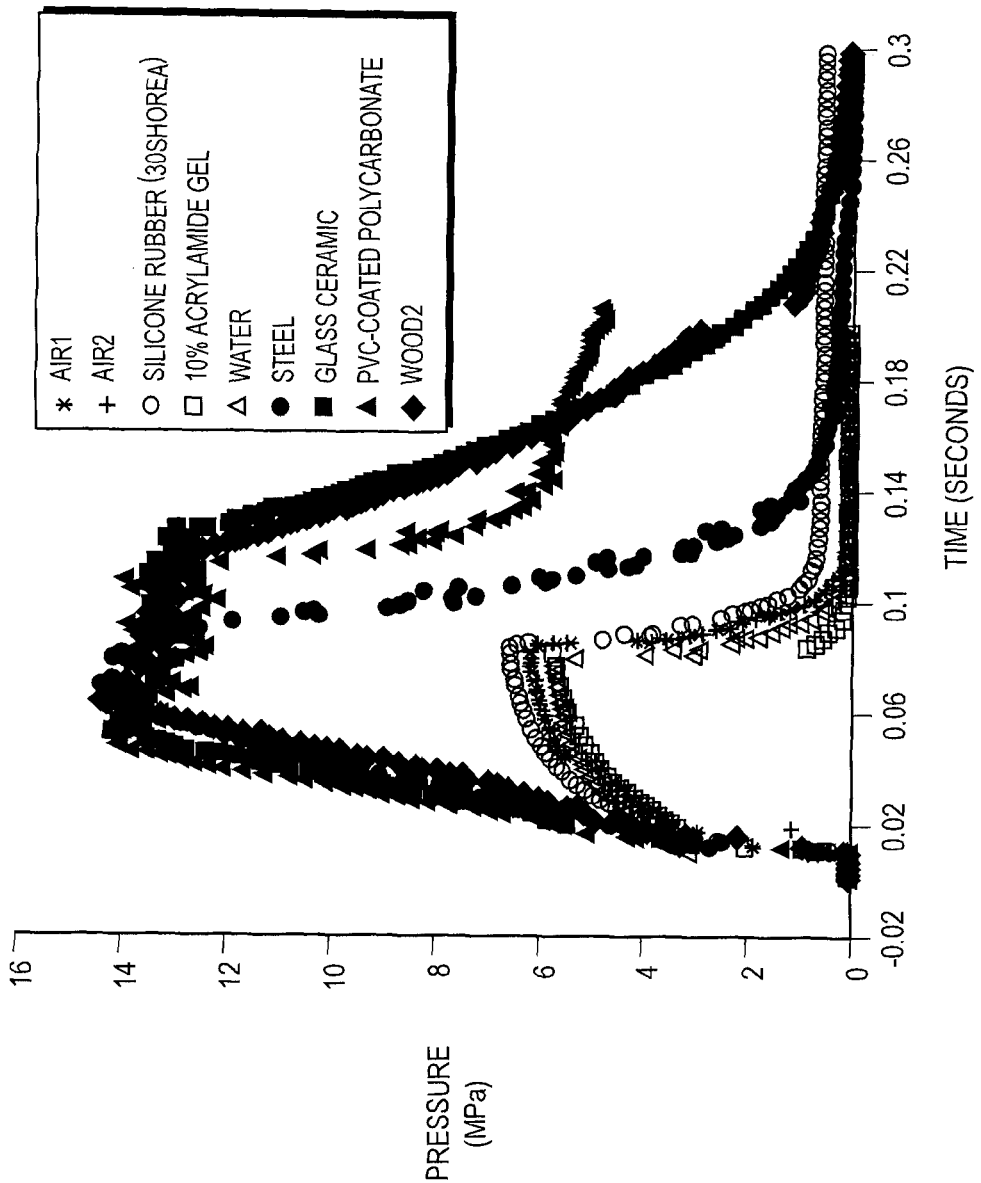
FIGS. 4A and 4B are graphs depicting pressure versus time, the measure being fluid pressure sensed using a strain gauge and a position sensor, respectively.
Figure 4B:
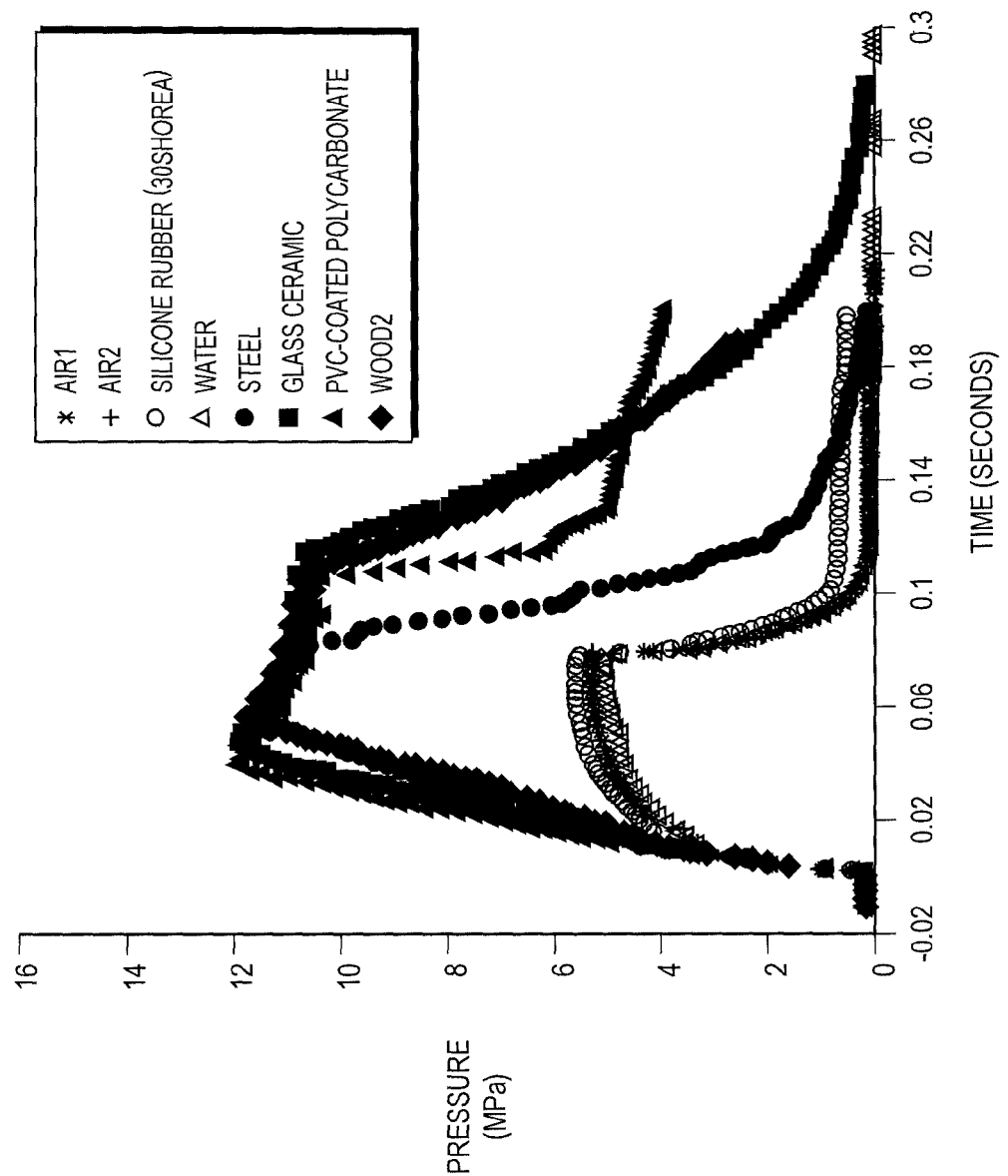

FIGS. 4A and 4B are graphs depicting pressure versus time of fluid pressure sensed using a strain gauge and a position sensor, respectively. The fluid pressure sensed comprises the pressure due the actuator ejecting the fluid through a nozzle and the back pressure from the fluid jet hitting the target material. Target materials include soft materials, including air (i.e., ejecting a fluid jet into air), silicone rubber (durometer 30 Shore A), 10% acrylamide gel, and water, as well as hard materials, including steel, glass ceramic, PVC-coated polycarbonate, and wood. Some of the target materials, such as the silicone rubber, are tissue analogs.

FIG. 4A shows the pressure sensed using a strain gauge 216F coupled to the ampoule 208. The strain gauge measures hoop stress of the ampoule during fluid ejection. FIG. 4B shows the pressure sensed using a linear encoder 216B that measures the position of the voice coil of the actuator 202, the position being related to the force applied by the actuator to the ampoule during fluid ejection. Both methods of sensing pressure produce pressure profiles that can be used to distinguish between hard and soft materials. Both methods may also be used to further distinguish among the tested materials in the hard and soft group of materials. The sensed difference in pressure profiles due to differences in material hardness is a material property, or surface condition, that can be used to control the ejection of fluid.

Figures 4C, 4D:
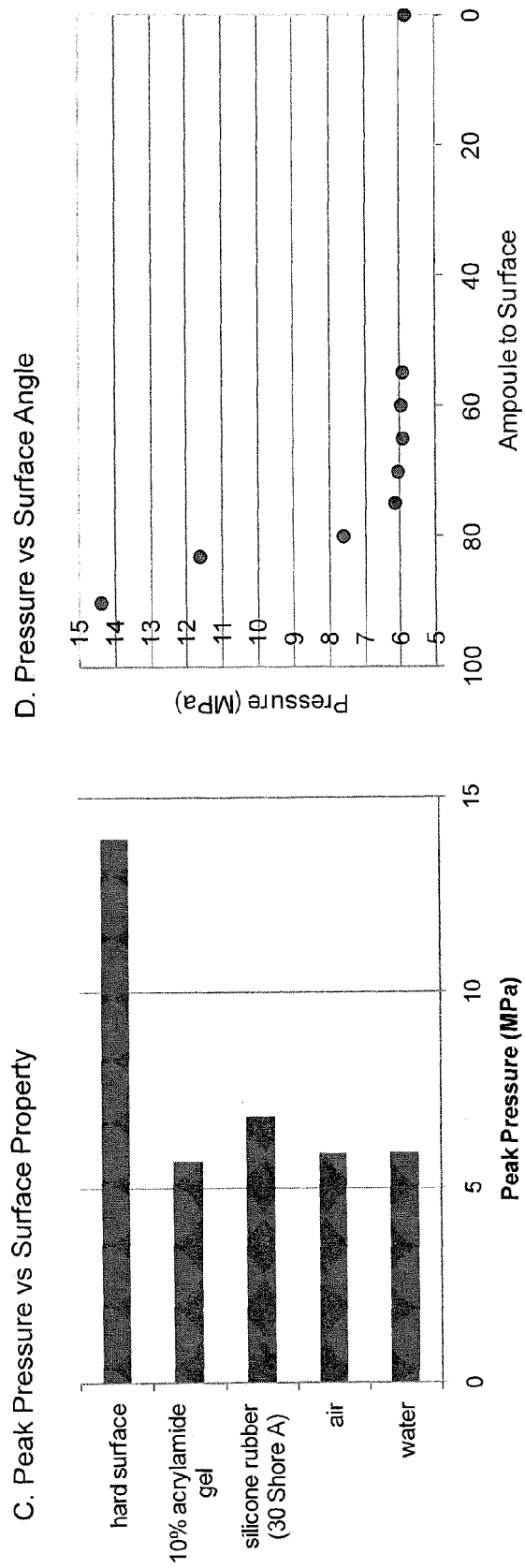
FIG. 4C is a graph of peak pressures sensed during ejection of fluid against materials of different surface properties.
FIG. 4D is a graph of pressure versus angle of injection against a surface.

FIG. 4C is a graph of peak pressure for ejection of fluid against materials of different surface properties. The value for the hard surface represents the average of the values obtained for all hard surfaces measured, including those described with reference to FIG. 4A. The sensed difference in peak pressure with different material hardness is a material property or surface condition that can be used to control the ejection of fluid.

FIG. 4D is a graph of pressure versus angle of injection against a hard surface, such as a glass ceramic or steel. The graph shows that peak pressure varies with the angle of injection, with the highest pressure measured at an angle of about 90 degrees and little variation in pressure for angles between about 80 and 0 degrees. The sensed difference in peak pressure with different ejection angles may be used to control the ejection of fluid.

Embodiments of the invention may employ a linear Lorentz-force actuator to propel liquid and/or medicant under pressure at specific sites along the tissue-tooth interface in order to expose, identify, and remove plaque from the tooth and gingival crevice with application to both professional and every day oral care. Medicant may be any of a number of antiseptics, anti-plaque agents, or biomarkers that can improve oral hygiene or aid in the diagnosis of local or systemic disorders.

In certain embodiments, a Lorentz-force actuator is used to propel liquid under pressure to the tissue/tooth interface. The device may be a multi-actuated device that will move along the gum line with the capability of differentiating between the soft and hard surfaces comprising the target area. The device may house one or more Lorentz-force actuators within a hand grip or housing. The device can be a single or multi actuated device with one or more of the following properties:

Be contiguous with a tip in fluid communication with the target (e.g., tissue/tooth interface) and a small fluid reservoir.

Be in communication with a probe that can be used to mechanically perturb the tissue/tooth interface and provide identification of tooth versus tissue within a 2-3 s time period. In one embodiment, the probe could be attached to a custom designed linear Lorentz-force actuator and used to apply a force (<5 N) to the tooth or gum surface (i.e. perturbing the surface). The tissue responsive to the perturbation can be displacement analyzed using stochastic system identification as described in Y. Chen and I. W. Hunter, In vivo characterization of skin using a Wiener non linear stochastic identification method. Proceedings of $31^{st}$ Annual IEEE Engineering in Medicine and Biology Conference, (2009) 6010-6013, and in U.S. Pending patent application Ser. No. 12/872,630, filed on Aug. 31, 2010, entitled "Nonlinear System Identification Techniques and Device For Discovering Dynamic And Static Tissue Properties", incorporated by reference in their entirety. More specifically, the system (i.e. the actuator, probe tip, and target) is excited using a Gaussian white noise voltage input which drives the actuator through a linear power amplifier. The actuator in turn imposes a force on the probe tip and by extension the target surface. Analysis of the output (i.e. tissue displacement) permits one to discriminate the hard tooth surface (high local stiffness) from the soft tissue or plaque (lower local stiffness). While mechanically attached to the front of the coil, the probe could maintain some degree of freedom for repositioning within/between the teeth. In another embodiment electrical impedance could be used to differentiate between tooth and gum.

Use one or more strain gauges, attached to the outer face of the ampoule but well within the volume window, to determine the deformation of the delivery housing (e.g. ampoule) with a constant input force (pressure) and variable surface; harder surfaces (e.g. tooth) exhibiting higher peak pressures than softer surfaces (e.g. gum).

Use light waves to differentiate between tooth and gum since the regular structure of tooth ensures good propagation through the enamel and tubules in the dentin. As such, changes in structure manifest as changes in scattering of light as it passes through the tooth and in changes in absorption and fluorescence on the surface of the tooth. These latter changes which are normally used to differentiate between healthy and caries ridden teeth can also be used to differentiate between tooth and gum. Techniques based on these interactions include, but are not limited to, multiphoton imaging, infrared thermography, infrared fluorescence, and optical coherence tomography (OCT). Of these techniques, OCT is most easily adapted for inclusion into the jet injection device.

Use an acoustic wave imposed on the fluid jet together with the actuation of the linear Lorentz-force actuator to determine the phase difference or time of flight and force respectively.

The pressure at which fluid is ejected from the tip is servo-controlled with delivery of fluid into the fluid reservoir and ejection through a narrow orifice (i.e. <500 μm) under pressure to deliver a high jet stream of fluid to the tooth-tissue interface. The pressure will be varied dependent on the interface. Prior to delivery the degree of pressure required will be determined by evaluating the plaque on tooth surfaces and gingiva using the jet injector.

In one embodiment, the jet injector is used to deliver disclosant dyes [D. A. Baab, A. H. Broadwell, and B. L. Williams, A comparison of antimicrobial activity of four disclosant dyes, J Dental Res 62 (1983) 837-841] to identify dental plaque. It is known that there are several dye indicators for dental plaque which include, but are not limited to, erythrosin (FCD Red #3) (U.S. Pat. No. 3,309,274), sodium fluorescein (FDC Yellow #8) [in H. Wolf, Color atlas of dental hygiene: periodontology (2006) 225-227], and betanin (U.S. Pat. No. 4,431,628).

In some embodiments, other methods may be used individually or in combination for plaque identification, including:

Various optical spectroscopic techniques (e.g. scattering, absorption, and fluorescence in the visible or infrared) which can be accomplished by shining a laser beam down the delivery channel when using a semi transparent jet of liquid. This can also include OCT technologies.

Raman spectroscopy or faster techniques such as coherent Raman, Coherent Anti-Stocks Raman Spectroscopy (CARS) (e.g. broadband, time resolved, frequency-modulated), and Optical Heterodyned-Detected Raman-Induced Kerr Effect (OHD-RIKE). These methods may also provide information relating to the microbial composition based on known or identified Raman spectra peaks.

Various sound wave technologies (e.g. ultrasound, elastography), where one can use the phase difference, time of flight, and reflection response peak intensities to distinguish plaque from tooth.

Nuclear Magnetic Resonance (NMR).

The above techniques singly or in combination may be coupled or combined with stochastic system identification techniques to determine differences in material properties. The state of the tooth/tissue interface, as detected by one or more of the above techniques, can be used to determine, in real time, the waveform required to mechanically remove plaque from the specific tooth tissue interface.

Plaque removal can be accomplished by delivery of a high pressure jet of fluid, such as water, medicant, or both. Medicant can include, but is not restricted to, chelating agents, fluoride (known to inhibit the ability of oral bacteria to create acid) or fluorescent dyes or probes used to detect bacterial specific changes (e.g. pH etc.) and/or biochemical specific biomarkers. Delivery of said medicants may also employ controlled release packaging such as gel like fluid, particles, or solids. Delivery of such medicants has been demonstrated by the ability of the ejector device to deliver colored beads to the subgingival space as described with reference to FIGS. 5A-5D. Several articles reviewing potential targets and the use of saliochemistry as a diagnostic tool have been published [J. K. M. Aps and L. C. Martens, Review: The physiology of saliva and transfer of drugs into saliva. Forensic Sci International 150 (2005) 119-131; F. M. L. Amado, R. M. P. Vitorino, P. M. D. N. Dominigues, M. J. C. Lobo, and J. A. R. Duarte, Analysis of the human saliva proteome, Exp Rev Proteomics 2 (2005) 521-539; B. J. Baum, A. Voutetakis, and J. Wang, Salivary glands: novel target sites for gene therapeutics, TRENDS Mol Med 10 (2004) 585-590; E. Kaufman and I. B. Lamster, The diagnostic applications of saliva—a review, Crit Rev Oral Biol Med 13 (2002) 197-212; A. Aguirre, L. A. Testa-Weintraub, J. A. Banderas, G. G. Haraszthy, M. S. Reddy, and M. J. Levine, Critical reviews in oral biology & medicine, Sialochemistry: A diagnostic tool 4 (1993) 343-350].

Figure 5A:
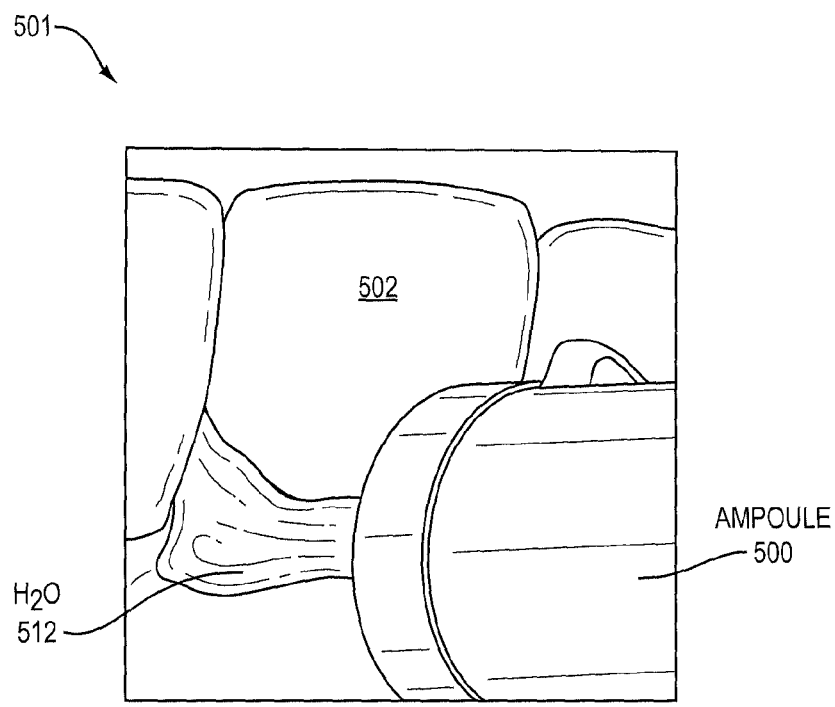
FIGS. 5A-5D are perspective diagrams showing delivery of water and black beads to the gum line and sulcus.
Figure 5B:
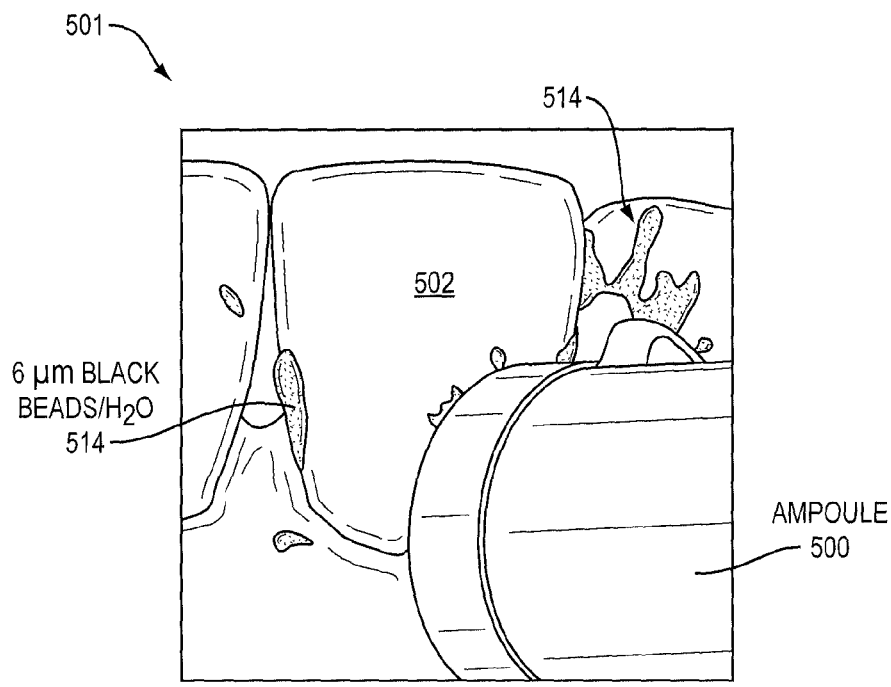
Figure 5C:
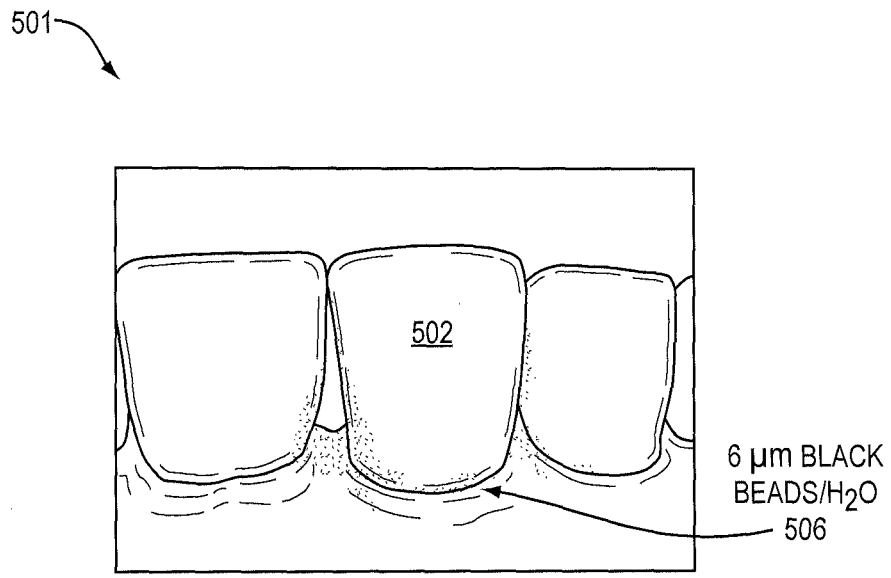
Figure 5D:
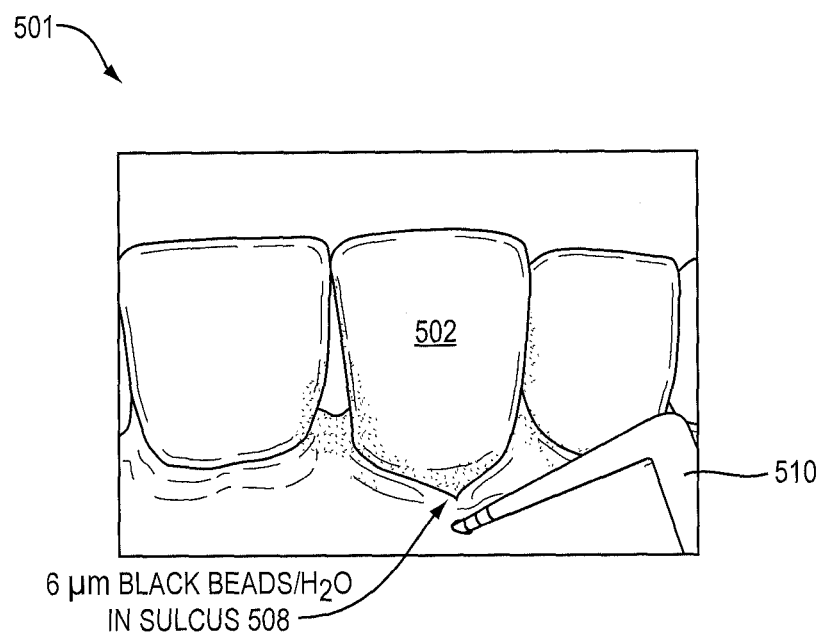

FIGS. 5A-5D show the delivery of water and 6 µm beads to the subgingival space using jet injector 500. Typodont and/or dentiform tooth and gum models can be used to evaluate the delivery of black polystyrene beads to the sulcus, which is the natural space between the tooth and the gum surface. FIG. 5A shows typodont 501, which is a model of the oral cavity, including teeth 502, gingival 504, and the palate (not shown). The typodont 501 can include polymers of different stiffness for the gingiva, or gums, 504. FIG. 5A shows the delivery of a continuous stream of water 512 to the tooth/gum interface of typodont model 501 using the jet injector 500. Only part of the jet injector, the distal end of the ampoule or reservoir, is visible. FIG. 5B shows the delivery beads 514 and water to the tooth/gum interface of the typodont model 501 using the jet injector. The delivery waveform was tailored to eject a solution of beads at 100 m/s for 10 seconds in order to separate the tooth and gum followed by delivery of the remaining solution at 10 m/s in order to deposit bead into the sulcus. FIG. 5C shows the typodont model 501 after delivery of beads to the gum line 506 using the jet injector. FIG. 5D shows the typodont model of FIG. 5C with the gum 504 partly pulled away by probe 510 to expose the beads delivered to the sulcus 508. Delivery of beads to the sulcus demonstrates the use of the jet injector, such as device 200 of FIG. 2A, for delivery of medicant to this area.

In some embodiments, identification and/or removal of plaque may be coupled with oral diagnostics, including, for example, detection or change in concentration of an analyte (e.g. antigen, antibody, nucleic acid etc.) in a fluid. The jet injector may be used to remove a small volume of saliva either pre- or post-brushing/cleaning to evaluate oral health and/or systemic health.

In one embodiment, the jet injector can be used to remove a small amount of fluid that would be mixed with a conjugated antibody (fluorescent, enzymatic etc.), and loaded into a microtiter plate, the wells of which contain antibody to the antigen(s) of interest. Binding would be detected by addition of an appropriate substrate.

In another embodiment, saliva may be collected into a modified, disposable tip lined with a solid support or matrix containing an antibody array. Detection would involve inclusion of a second, specific labeled antibody or enzyme-antibody conjugate with subsequent substrate. Unbound analyte and binding reagent would be removed by delivery and removal of a wash solution after each binding reaction using the bi-directionality of the linear Lorentz-force actuator.

Figure 6:
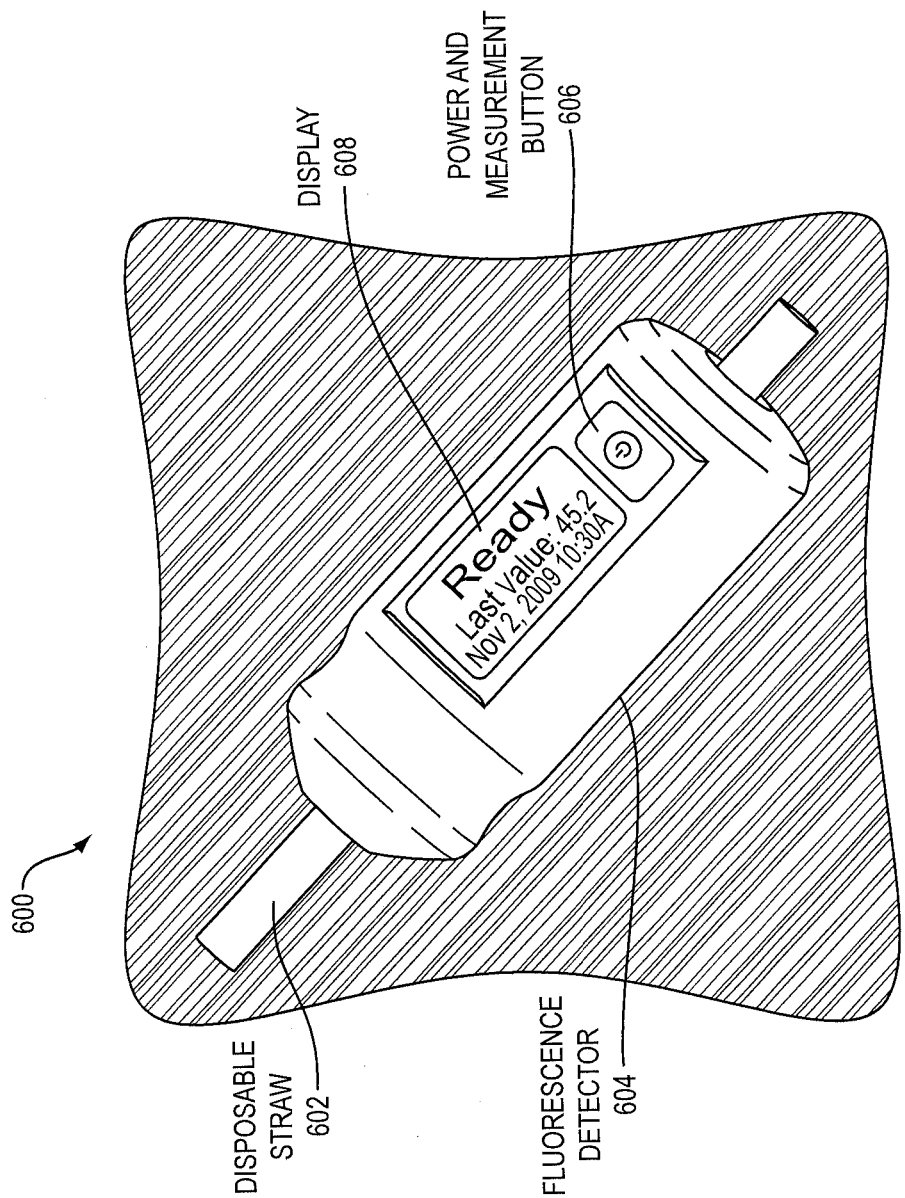
FIG. 6 is a top perspective diagram of an exemplary detector for detecting an analyte from a sample collected in a disposable tube.

FIG. 6 shows an exemplary device 600 for detecting an analyte from a sample collected in a disposable tube. The device uses a disposable, spherical tube (e.g. straw) 602 for the collection of saliva. After collection, the tube is placed within a non-disposable detector or analyzer 604. In one embodiment, fluid, such as saliva, may be deposited or drawn directly into a disposable, spherical tube 602, using the jet injector device, reacted with specific, labeled or conjugated binding reagent (e.g. fluorophore or enzymatic respectively) dried onto the inner surface of the straw at a specific location, and then absorbed onto a solid support or matrix, for example a polymer, containing one or more antibodies of interest bound at a specific site. At this point, the straw 602, if still attached to the jet injector device, can be removed and slid into the non-disposable detector 604. Unbound analyte and binding reagent may be removed by passage of a wash solution through the straw followed by substrate if using an enzyme conjugate. The device 600 may include user controls, such as power button 606, to start and control the analysis and measurement. A display 608 may also be included to display the results of the measurement to the user. Detector or analyzer 604 may, for example, include detector 1000 described with reference to FIG. 10.

In some embodiments, a detector or analyzer, such as detector 600, may be integrated into the jet injector. As shown in FIG. 1, optional detector or analyzer 122 may be coupled to or included in the needle-free injector 100 to detect a marker of oral health using the analyzer 122. The injector 100 may control ejection of a substance against tooth or gum responsive to the detected marker. In one embodiment, the jet injector uses a Lorentz-force actuator to eject the substance, which may be fluid or a fluid containing a medicant. Because the Lorentz-force actuator is bi-directional, depending upon the direction of the coil current, the same device used to inject a substance can also be used to withdraw a sample. This is a beneficial feature as it enables the device to collect a sample.

Figure 7A:
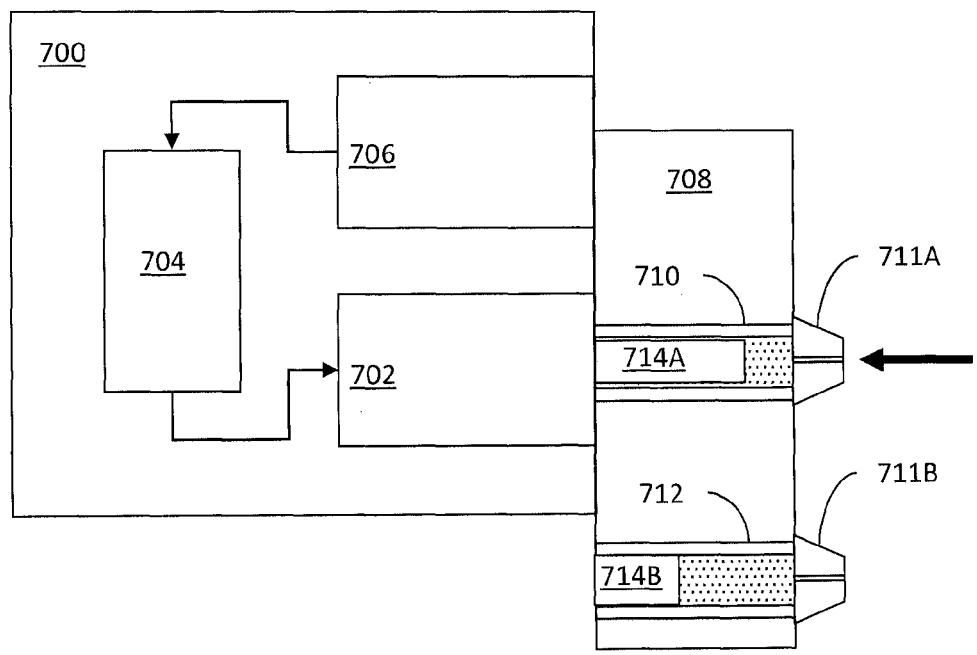
FIGS. 7A and 7B are schematic block diagrams of a needle-free transport device providing sampling and analysis capability, respectively shown in the sampling and fluid ejection configurations.

Referring to FIG. 7A, an exemplary sampling, needle-free injector 700 is illustrated. The sampling jet injection device 700 includes a bi-directional electromagnetic actuator 702 abutting at one end a first piston 714A. A sampling nozzle 711A is coupled at the other end of a syringe or ampoule 710. The actuator 702 is controlled by controller 704. Controller may include a power source (not shown), such as a battery or suitably charged storage capacitor, to power the actuator 702. The first piston 714A is slidably disposed within a sampling syringe 710, such that an electrical input signal applied to the actuator 702 withdraws the first piston 714A away from the sampling nozzle 711A. A sample can be collected from an oral cavity or a surface when the sampling nozzle 711A is placed in the oral cavity or near the surface during actuation. Collecting a sample may include first ejecting a substance into the oral cavity or against a surface and then withdrawing a sample that includes at portion of the ejected substance and a biological sample, e.g., a biological fluid.

Figure 7B:
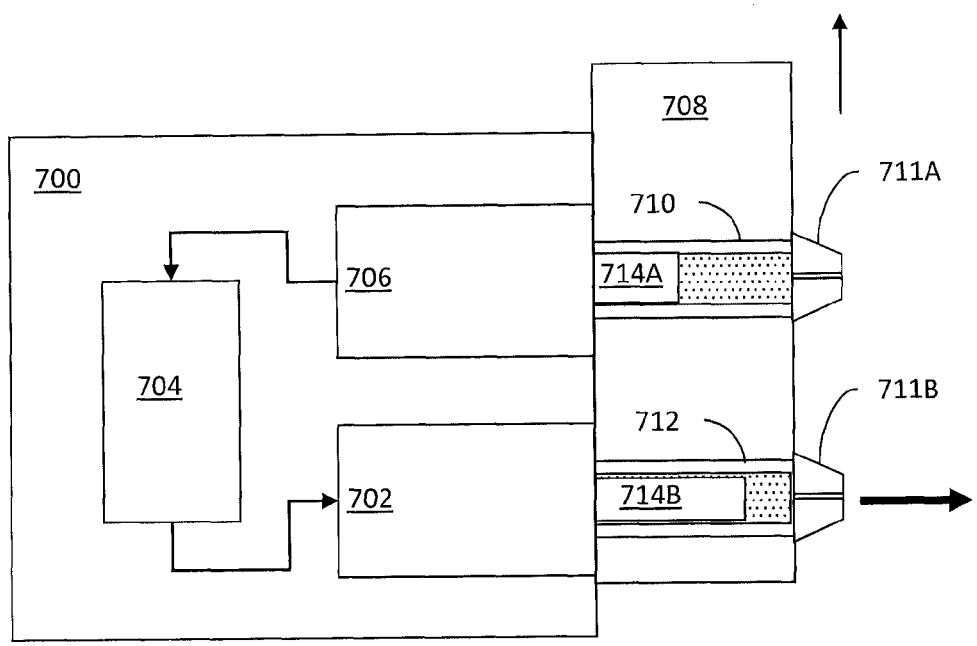

Referring now to FIG. 7B, once a sample has been collected, a movable syringe mount 708 can be re-positioned such that the sampling syringe 710 is aligned with an analyzer or detector 706. By the same motion, a second syringe 712 having a second piston 714B and including a substance, such as a fluid, cleansing agent, or medicant, is aligned with the actuator 702. The mount 708 may be a rotary mount rotating about a longitudinal axis or a linear mount as shown. The analyzer or detector 706 provides a control signal to the controller 704 responsive to the analyzed sample. The control signal, via controller 704, causes the actuator 702 to push the second piston 714B forward thereby expelling an amount of the substance responsive to the analyzed sample. Thus, the same device 700 can be used to both collect a sample and to eject a substance. In an embodiment, the jet injector device may include two jet injectors and/or actuators, one to sample and the other to eject a substance responsive to the analyzed sample.

Figure 8:
FIG. 8 is a top perspective diagram of an exemplary detector for detecting an analyte using a polymer strip.

In yet another embodiment, a polymer strip containing plaque-specific biomarkers, for example *Streptococcus* species, is attached to a disposable head of a tooth brush or tooth brush-like device. FIG. 8 shows an example of a disposable, polymer strip 802 containing a plaque-specific biomarker attached to the head of a toothbrush or toothbrush-like device 800. The strip 802 can be attached to or included in a disposable top section 810 or device 800. The strip 802 may be coupled to or in fluid communication with a sensor section 804 of device 800 via top section 810. When inserted into the mouth, the polymer strip will absorb saliva and bind analyte(s) of interest. The strip can then be peeled away and processed as above or the strip can be analyzed by sensor 804 on the device itself. For example, binding of an analyte of interest, such as a plaque-specific biomarker, can be determined by a change in impedance. Binding of an analyte can also be determined by a change in absorbance or fluorescence, as for example by enzyme linked immunoabsorbant assay (ELISA). The device can include a power and measurement button 806 to initiate the analysis. A display 808 may be included to display results of the analysis to a user.

The above embodiments may be configured or modified to detect changes in antibody concentration, for example IgA, a common component of the mucosal immune system. In this case, the analyte would bind to a specific antigen with detection by a labeled secondary antibody, as for example described below with reference to FIGS. 9A-9B and FIG. 10.

Figure 9A:
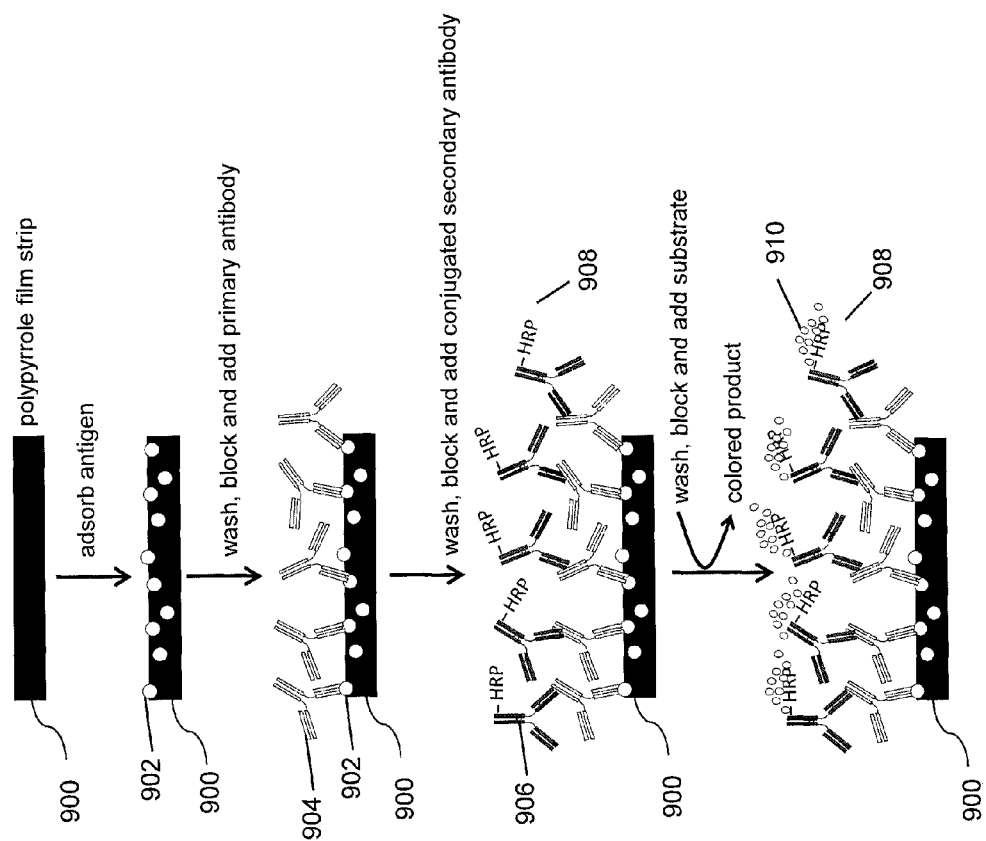
FIG. 9A is a schematic diagram showing binding of an analyte (antibody) to a solid support (polypyrrole film strip)
Figure 9B:
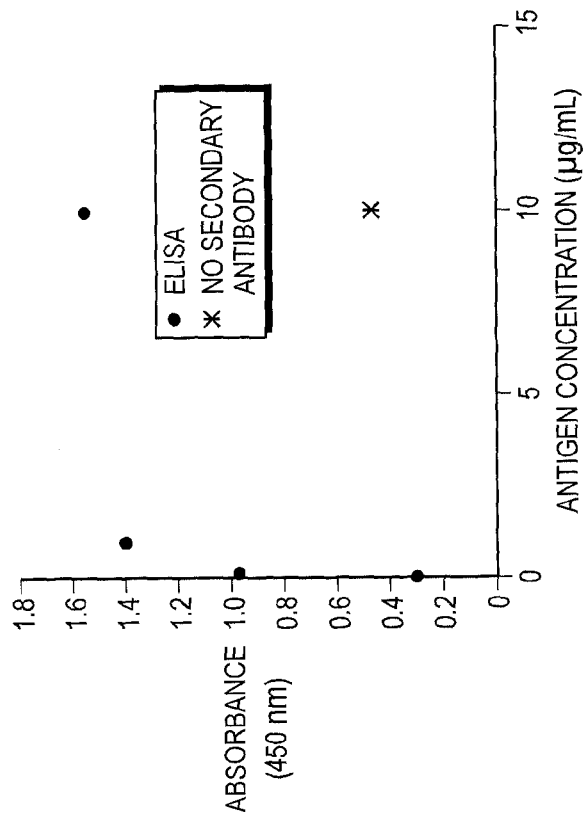
FIG. 9B is a graph of light absorbance versus antigen concentration.

FIGS. 9A-9B illustrate the use of disposable, polymeric strips to evaluate oral health status. FIG. 9A is schematic diagram showing binding of an analyte 904 (in this case antibody) to a solid support 900 (in this case a polypyrrole film strip) to which antigen 902, specific to the analyte of interest, can be adsorbed, entrapped, or covalently attached. Prior to the addition of analyte, unbound antigen is removed by washing and free sites on the polymer strip blocked to prevent non-specific binding of successive reagents. Addition of analyte 906 followed by washing and blocking prior to the addition of labeled secondary antibody specific to the analyte. The secondary antibody may be conjugated to a fluorophore or enzyme, for example horseradish peroxidase (HRP) 908 as shown. In this latter case, binding is detected by the addition of a substrate 910 that, in the presence of HRP, yields a colored product that can be detected by reading absorbance. Alternatively, binding of primary antibody could be detected by measuring a change in electrical impedance. FIG. 9B is a plot of ELISA results showing increase in absorbance observed with absorption of increasing concentrations of antigen into polypyrrole film strips.

Figure 10:
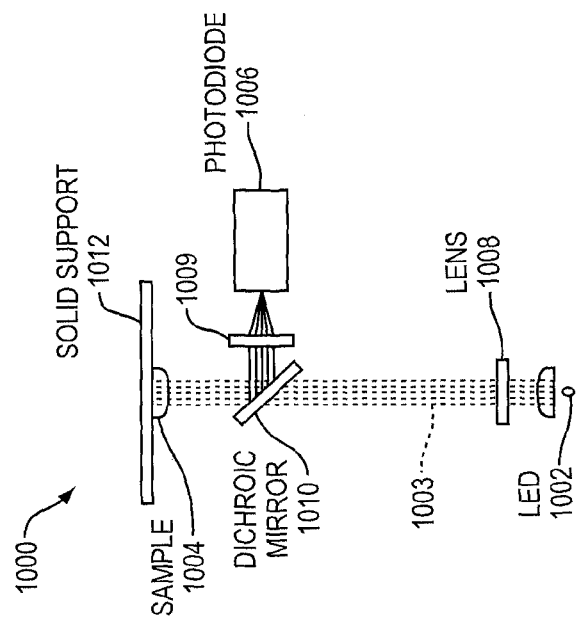
FIG. 10 is a schematic diagram showing a detector for detecting a marker or analyte of oral health status.

FIG. 10 is a schematic diagram showing a detector for detecting a marker or analyte of oral health status, such as a labeled or conjugated antibody shown in FIG. 9A. The detector 1000 consists of a light source 1002 that excites the sample 1004 with light 1003, and photodiode 1006 to measure the light emitted from the sample. Sample 1004 includes the marker or analyte of interest. Detector 1000 further includes a lens 1008 to focus the light of the light source 1002 on the sample 1004, and a dichroic mirror 1010 to reflect the light emitted from the sample through a second lens 1009 and into the photodiode 1006. Light source 1002 may include a light-emitting diode (LED). Sample 1004 may be supported by or deposited on a solid support 1012, which may include a polymer strip, such as strip 900 described with reference to FIG. 9A.

Alternatively or in addition to optical detection, binding of a marker or analyte may also be detected using electrical impedance. Furthermore, saliva samples obtained using the jet injector could be processed directly using Coherent Raman spectroscopy.

The devices and techniques described herein provide a means of quantifying specific bacterium, antibody, etc. relevant to oral health and disease and thereby a means of determining effective and appropriate intervention strategies.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of tooth treatment comprising:
    sensing a surface condition of tooth or gum using a sensor that senses a signal reflected from tissue back through a liquid jet, the signal propagating only through the liquid jet between a liquid ejector and the tissue, the liquid jet being a continuous stream of uninterrupted liquid between the liquid ejector and the tissue; and
    with a servo-controller, controlling ejection of the liquid jet against the tooth based on the sensed condition, wherein the liquid is ejected by means of the liquid ejector comprising a Lorentz-force electromagnetic actuator including a magnet assembly providing a magnetic field and a coil assembly.

2. The method of claim 1 wherein the liquid is carried in a self-contained reservoir in a handle of a liquid ejection device.

3. The method of claim 2 wherein the reservoir is less than 100 milliliters.

4. The method of claim 1 wherein the liquid is a cleansing solution.

5. The method of claim 1 wherein the liquid contains cleaning particles.

6. The method of claim 1 wherein the jet is of a diameter of less than 500 microns.

7. The method of claim 1 wherein the jet is of a diameter of less than 200 microns.

8. The method of claim 1 wherein the ejection is controlled at a bandwidth of at least 10 hertz.

9. The method of claim 1 wherein the ejection is controlled at a bandwidth of at least 50 hertz.

10. The method of claim 1 wherein the ejection is controlled at a bandwidth of at least 100 hertz.

11. The method of claim 1 wherein the ejection is controlled at a bandwidth of at least 1 kilohertz.

12. The method of claim 1 wherein the liquid is ejected at a peak relative pressure of at least 1 kilopascal.

13. The method of claim 1 wherein the liquid is ejected at a peak relative pressure of at least 100 kilopascals.

14. The method of claim 1 wherein the liquid is ejected at velocity of at least 1 meter per second.

15. The method of claim 1 wherein the liquid is ejected at velocity of at least 10 meters per second.

16. The method of claim 1 wherein the ejection is controlled to clean teeth at high pressure and to reduce pressure applied to gum.

17. The method of claim 16 wherein the ejection is controlled to clean plaque.

18. The method of claim 16 wherein less than 100 milliliters of liquid is ejected per teeth cleaning session.

19. The method of claim 1, wherein controlling ejection of the liquid jet against the tooth further includes controlling ejection of the liquid jet against the tooth to remove soft tooth.

20. The method of claim 1 further comprising automatically scanning the liquid jet relative to a handle of an injection device.

21. The method of claim 1 wherein the magnet assembly is a stationary magnet assembly and the coil assembly is slidably disposed with respect to the magnet assembly, the coil assembly driving ejection of the liquid jet.

22. The method of claim 1 wherein sensing the surface condition comprises measuring a response of tissue to a mechanical perturbation.

23. The method of claim 22 wherein the mechanical perturbation comprises applied force and the measured response comprises deformation of the tissue.

24. The method of claim 22 further comprising mechanically disturbing the tissue with the liquid jet.

25. The method of claim 22 wherein measuring a response comprises measuring pressure of the liquid.

26. The method of claim 25 wherein measuring pressure comprises sensing strain of a liquid reservoir.

27. The method of claim 25 wherein measuring pressure comprises sensing position of the actuator driving the ejection of the liquid.

28. The method of claim 1 wherein sensing the surface condition comprises sensing an acoustic signal reflected from tissue.

29. The method of claim 28 wherein the acoustic signal is sensed using a piezo-electric transducer.

30. The method of claim 28 further comprising generating the acoustic signal.

31. The method of claim 30 wherein the acoustic signal is generated and sensed using a piezo-electric transducer.

32. The method of claim 28 wherein the acoustic signal comprises a stochastic signal.

33. The method of claim 28 wherein sensing the surface condition further comprises measuring tissue deformation with applied force using the sensed acoustic signal.

34. The method of claim 33 wherein the force is applied using the liquid jet.

35. The method of claim 1 further comprising sensing motion of the liquid ejector and controlling the ejection of the liquid jet based on the sensed motion.

36. A method of tooth treatment comprising:
ejecting a liquid jet against the tooth by means of a liquid ejector comprising a Lorentz-force electromagnetic actuator including a magnet assembly providing a magnetic field and a coil assembly, the liquid jet being a continuous stream of uninterrupted liquid between the liquid ejector and the tooth, the stream having a diameter of less than 500 microns, a peak relative pressure of at least 1 kilopascal and up to 100 megapascals, and velocity of at least 1 meter per second and up to 226 meters per second;
sensing a surface condition of tooth or gum using a sensor that senses a signal reflected from tissue back through the liquid jet, the signal propagating only through the liquid jet between the liquid ejector and the tissue; and
with a servo-controller, controlling ejection of the liquid jet based on the sensed surface condition.

37. The method of claim 36 wherein the liquid is carried in a self-contained reservoir in a handle of a liquid ejection device.

38. The method of claim 37 wherein the reservoir is less than 100 milliliters.

39. The method of claim 36 wherein the jet is of a diameter of less than 200 microns.

40. The method of claim 36 wherein the liquid is ejected at a peak relative pressure of at least 100 kilopascals and up to 100 megapascals.

41. The method of claim 36 wherein the liquid is ejected at velocity of at least 10 meters per second and up to 226 meters per second.

42. The method of claim 36 wherein the liquid jet is controlled at a bandwidth of at least 10 hertz.

43. The method of claim 36 wherein the liquid jet is controlled at a bandwidth of at least 50 hertz.

44. The method of claim 36 wherein the liquid jet is controlled at a bandwidth of at least 100 hertz.

45. The method of claim 36 wherein the liquid jet is controlled at a bandwidth of at least 1 kilohertz.

46. The method of claim 36, wherein the tooth treatment is for removing plaque from teeth.

47. The method of claim 36 further comprising automatically scanning the liquid jet relative to a handle of an injection device.

48. The method of claim 36 wherein the magnet assembly is a stationary magnet assembly and the coil assembly is slidably disposed with respect to the magnet assembly, the coil assembly driving ejection of the liquid jet.

49. A hand-held tooth treatment device comprising:
a housing configured to be held in hand;
a liquid ejector comprising a Lorentz-force electromagnetic actuator including a magnet assembly providing a magnetic field and a coil assembly, the Lorentz-force liquid ejector positioned at an end of the housing and ejecting a liquid jet against the tooth in a scanning movement relative to the housing, the liquid jet being a continuous stream of uninterrupted liquid between the liquid ejector and the tooth;
a transducer generating a signal, the signal propagating only through the liquid jet between the liquid ejector and the tissue;
a sensor that senses a reflected signal reflected from tissue back through the liquid jet, the reflected signal propagating only through the liquid jet between the liquid ejector and the tissue; and
a servo controller controlling pressure of ejected liquid in response to a sensed surface condition, the surface condition being sensed based on the reflected signal.

50. The device of claim 49 further comprising a self-contained reservoir of the liquid in the housing.

51. The device of claim 50 wherein the reservoir is less than 100 milliliters.

52. The device of claim 49 wherein the scanning movement is greater than 1 millimeter.

53. The device of claim 49 wherein the sensed surface condition comprises a mechanical property of tissue.

54. The device of claim 49 wherein the sensor is a pressure sensor that senses pressure of the liquid in the ejector.

55. The device of claim 54 wherein the pressure sensor comprises a strain gauge that senses strain of a reservoir of the ejector.

56. The device of claim 49 wherein the sensor is a proximity sensor that senses distance of the ejector from a tissue surface.

57. The device of claim 56 wherein the proximity sensor comprises a piezo-electric transducer and the distance is sensed using an acoustic signal.

58. The device of claim 49 further comprising the servo controller controlling pressure of the ejected liquid jet in response to a sensed motion of the ejector.

59. A method of tooth treatment comprising:
    ejecting a liquid jet against the tooth using a liquid ejector comprising a Lorentz-force electromagnetic actuator including a magnet assembly providing a magnetic field and a coil assembly, the liquid jet being a continuous stream of uninterrupted liquid between the liquid ejector and the tooth;
    scanning the liquid jet relative to a handle of the ejector;
    sensing a surface condition of tooth or gum using a sensor that senses a signal reflected from tissue back through the liquid jet, the signal propagating only through the liquid jet between the liquid ejector and the tissue; and
    with a servo-controller, controlling pressure of ejected liquid during scanning, based on the sensed surface condition.

60. The method of claim 59 further comprising controlling pressure of ejected liquid based on a sensed motion of the ejector.

61. The method of claim 59, wherein the tooth treatment is for removing plaque from teeth.

62. A tooth treatment device comprising:
    a liquid ejector that ejects a liquid jet against teeth, the liquid jet being a continuous stream of uninterrupted liquid between the liquid ejector and the teeth, the liquid ejector comprising a Lorentz-force electromagnetic actuator including a magnet assembly providing a magnetic field and a coil assembly;
    a transducer generating a signal, the signal propagating only through the liquid jet between the liquid ejector and the tissue;
    a sensor that senses a reflected signal reflected from tissue back through the liquid jet, the reflected signal propagating only through the liquid jet between the liquid ejector and the tissue; and
    a servo controller controlling pressure of ejected liquid in response to a sensed surface condition, the surface condition being sensed based on the reflected signal.

63. The device of claim 62 further comprising a housing configured to be held in hand, the liquid ejector being positioned at an end of the housing.

64. The device of claim 63 further comprising a self-contained reservoir of the liquid in the housing.

65. The device of claim 64 wherein the reservoir is less than 100 milliliters.

66. The device of claim 62 wherein the sensed surface condition comprises a mechanical property of tissue.

67. The device of claim 62 wherein the sensor is a pressure sensor that senses pressure of the liquid in the ejector, and wherein the surface condition is sensed based on pressure sensed by the pressure sensor.

68. The device of claim 62 wherein the sensor is an acoustic transducer that senses an acoustic signal reflected off tissue, and wherein the surface condition is sensed based on the reflected acoustic signal.

69. A tooth treatment device comprising
    a liquid ejector that ejects a liquid jet against the tooth, the liquid jet being a continuous stream of uninterrupted liquid between the liquid ejector and the tooth, the stream having a diameter of less than 500 microns, a peak relative pressure of at least 1 kilopascal and up to 100 megapascals, and velocity of at least 1 meter per second and up to 226 meters per second, the liquid ejector comprising a Lorentz-force electromagnetic actuator including a magnet assembly providing a magnetic field and a coil assembly;
    a sensor that senses a signal reflected from tissue back through the liquid jet, the signal propagating only through the liquid jet between the liquid ejector and the tissue; and
    a servo controller controlling pressure of the ejected liquid jet in response to a sensed surface condition, the surface condition being sensed based on the reflected signal.

70. The device of claim 69 wherein the sensed surface condition comprises a mechanical property of tissue.

71. The device of claim 69 wherein the sensor is an acoustic transducer that senses an acoustic signal reflected off tissue, and wherein the surface condition is sensed based on the reflected acoustic signal.

72. The device of claim 69 further comprising a housing configured to be held in hand, the liquid ejector being positioned at an end of the housing.

73. The device of claim 72 wherein the liquid is ejected in a scanning movement relative to the housing.

* * * * *